(12) United States Patent
Gonen Williams et al.

(10) Patent No.: US 8,592,511 B2
(45) Date of Patent: Nov. 26, 2013

(54) SYNTHESIS, CAPPING AND DISPERSION OF NANOCRYSTALS

(75) Inventors: Zehra Serpil Gonen Williams, Lanham, MD (US); Yijun Wang, Greenbelt, MD (US); Robert J. Wiacek, Silver Spring, MD (US); Xia Bai, Olney, MD (US); Linfeng Gou, Greenbelt, MD (US); Selina I. Thomas, Hyattsville, MD (US); Wei Xu, Greenbelt, MD (US); Jun Xu, Frederick, MD (US); Rakesh Patel, Lawrenceville, NJ (US)

(73) Assignee: Pixelligent Technologies, LLC, Baltimore, MD (US)

( * ) Notice: Subject to any disclaimer, the term of this patent is extended or adjusted under 35 U.S.C. 154(b) by 58 days.

(21) Appl. No.: 13/064,905

(22) Filed: Apr. 25, 2011

(65) Prior Publication Data

US 2012/0088845 A1    Apr. 12, 2012

Related U.S. Application Data

(60) Provisional application No. 61/327,313, filed on Apr. 23, 2010, provisional application No. 61/407,063, filed on Oct. 27, 2010.

(51) Int. Cl.
*C08K 3/18* (2006.01)
*A61K 47/32* (2006.01)

(52) U.S. Cl.
USPC ........................................ 524/432; 514/772.4

(58) Field of Classification Search
USPC ......................................................... 524/432
See application file for complete search history.

(56) References Cited

U.S. PATENT DOCUMENTS

| 7,758,977 | B2 * | 7/2010 | Seal et al. | 428/698 |
| 8,337,788 | B2 | 12/2012 | Chaput et al. | |
| 2008/0124268 | A1 * | 5/2008 | Yang et al. | 423/511 |
| 2008/0264479 | A1 * | 10/2008 | Harris et al. | 136/255 |
| 2009/0220792 | A1 * | 9/2009 | Ying et al. | 428/403 |
| 2009/0233090 | A1 * | 9/2009 | Wong et al. | 428/338 |

FOREIGN PATENT DOCUMENTS

WO    WO 2011/133228 A3    10/2011

OTHER PUBLICATIONS

Notification of Withdrawal of International Application or Designations dated Nov. 8, 2011, issued in connection with PCT/US2011/000724.
Gao et al, "Influence of some parameters on the synthesis of $ZrO_2$ nanoparticles by heating of alcohol-aqueous salt solutions", Journal of Nanoparticle Research 1:349-352, 1999.
Garnweitner et al, "Large-Scale Synthesis of Organophilic Zirconia Nanoparticles and their Application in Organic-Inorganic Nanocomposites for Efficient Volume Holography", Small, 2007, vol. 3, No. 9, pp. 1626-1632.
International Preliminary Report on Patentability dated Oct. 23, 2012, issued in connection with PCT/US2011/000724.
Written Opinion dated Feb. 8, 2012, issued in connection with PCT/US2011/000724.

* cited by examiner

*Primary Examiner* — Hui Chin
(74) *Attorney, Agent, or Firm* — Nixon & Vanderhye P.C.

(57) ABSTRACT

Preparation of semiconductor nanocrystals and their dispersions in solvents and other media is described. The nanocrystals described herein have small (1-10 nm) particle size with minimal aggregation and can be synthesized with high yield. The capping agents on the as-synthesized nanocrystals as well as nanocrystals which have undergone cap exchange reactions result in the formation of stable suspensions in polar and nonpolar solvents which may then result in the formation of high quality nanocomposite films.

38 Claims, 14 Drawing Sheets

SYNTHESIS, CAPPING AND DISPERSION OF NANOCRYSTALS

The present application claims benefit of U.S. Provisional Application Nos. 61/327,313 and 61/407,063, filed Apr. 23, 2010 and Oct. 27, 2010, respectively, the entire contents of each of which is incorporated herein by reference.

STATEMENT REGARDING FEDERALLY SPONSORED RESEARCH OR DEVELOPMENT

This work was supported in part by Department of Commerce Cooperative Agreement Nos. 70NANB7H7014 and 70NANB10H012 and the National Science Foundation grant no. 0724417.

TECHNICAL FIELD

Preparation of capped colloidal semiconductor nanocrystals and their dispersions in polymeric solutions and films are described herein. The colloidal semiconductor nanocrystals are highly monodisperse with nanocrystal size between 1-10 nm. Nanocomposites having a high loading density of uniformly dispersed capped semiconductor nanocrystals incorporated therein may be formed with these nanocrystals. Suspensions of nanocrystals may be formed in various solvents and nanocomposites made of same may be made optically transparent with very little or no scattering.

Nanocrystals are single crystals of a material in which at least one dimension of the crystal is less than 1 micron in size. Nanocrystals may either retain the optical, mechanical, and physical properties of their bulk counterparts or display properties which are quite different. Nanocrystals can be made by a wide variety of methods, some of which include: liquid synthesis, solvothermal synthesis, vapor phase synthesis, aerosol synthesis, pyrolysis, flame pyrolysis, laser pyrolysis, ball-milling, and laser ablation.

Nanocrystals can be dispersed into a variety of media or combination of media, including, but not limited to: liquids, gels, glasses, polymers and solids. The dispersed nanocrystals may impart all or some of the properties of the nanocrystals upon the dispersion or may give the dispersion properties which are different from any of the individual components. The quality of the dispersion created between the nanocrystals and the media can have a large effect on the properties of the final dispersion. The quality of the dispersion of the nanocrystals in a medium can be described as being governed by complex interactions between a set of parameters, which include, but are not limited to: the chemistry of the nanocrystal surface (or the effective nanocrystal surface), the size and shape of the nanocrystals, the physical properties of the nanocrystals, the chemistry of the dispersion media, and the physical properties of the dispersion media. Well-dispersed nanocrystals can be defined as nanocrystals which are uniformly distributed throughout the media with a minimal amount of nanocrystal aggregates present. If the nanocrystals are not well-dispersed in the medium, the optical, mechanical, and physical properties of the nanocrystals may be altered or the properties of the media may be adversely affected.

Nanocomposites are nanocrystal dispersions composed of nanocrystals dispersed in a matrix including: polymers, ceramics and glasses. Nanocomposites can be made by the mixing of nanocrystals, either in powder form or already dispersed in another media, with precursor components of the matrix. A non-exhaustive list of potential matrix components for use in the formation of nanocomposites includes: monomers, oligomers, polymers, pre-polymeric resins, ceramics, pre-ceramics and glasses. Nanocomposites can be considered to be an extension of the well-known field of composites, where the micron-sized, or larger, fillers used in composites have been replaced by nanocrystals. In both composites and nanocomposites it may be possible to modify the optical, mechanical, and physical properties of the nanocomposites with the filler materials, but the reduced size of the fillers used in nanocomposites may result in relatively fewer, or less intense, detrimental effects due to the inclusion of a filler into the matrix. A list of these potentially detrimental effects which may happen to the composite include: reduced structural integrity, reduced mechanical strength, reduced mechanical stability, reduced flexibility, reduced optical transparency, and reduced thermal stability. To more fully realize the potential of using nanocrystals as replacements for micron size, or larger, fillers, the nanocrystals need to be able to be well-dispersed in the matrix. This is due to the fact that aggregated nanocrystals in the composite act as detrimentally as, or worse than, fillers of the size of the aggregates. Thus a composite made of heavily aggregated 5 nm particles, where the size of the aggregates are greater than 1 micron in all dimensions may not behave as a nanocomposite.

Typical routes for the manufacture of nanocomposites often result in a distribution of nanocrystals in the media that cannot be described as well-dispersed. The distribution of the nanocrystals is often non-uniform and contains large amounts of aggregates. One key to producing well-dispersed nanocomposites is to use nanocrystals which are not aggregated before the start of mixing with the matrix or media.

There are two main types of aggregates that are often discussed in literature. Hard aggregates are clusters of nanocrystals, in which the nanocrystals are relatively strongly bound to each other. Hard aggregates may be the result of particles that have come into contact during formation or after formation but while the materials are still at elevated temperatures. The other type of aggregates, soft aggregates, is usually formed after synthesis, or at lower temperatures. The conventional wisdom is that soft aggregates can be broken apart easily during processing and can thus be made to be well-dispersed, whereas hard aggregates cannot be broken apart without great difficulty and therefore are not suitable sources of well-dispersed nanocrystals. In order to form dispersions in which the nanocrystals are well dispersed, it is preferable to avoid both types of aggregation.

Nanocrystal aggregation is controlled by the surface chemistry (or chemistry of the effective surface) of the nanocrystals. In a dispersion, the inter-particle forces (such as electrostatic forces, van der Waals forces and entropic forces) between the surfaces of the nanocrystals result in a tendency to form aggregates. These inter-particle forces are particularly important in nanocrystals because of the large surface to volume ratio for these particles. In order to avoid aggregation in dispersion it is desirable for the surfaces of the nanocrystals to be passivated (or stabilized). One method that may be used to passivate the surface of the nanocrystal involves the introduction of ligand ions or molecules. These ligands, which are also called capping agents or caps, are added to the surface of the nanocrystals and thus create a new effective surface of the nanocrystals. This effective surface is the surface of the shell created by the complete or partial surface coverage with ligands. The chemistry of this effective surface can be tailored in order to create a chemical environment, distinct from the actual or initial surface of the nanocrystal, which facilitates dispersion while preventing or reducing aggregation. These passivating ligands can help prevent aggregation in a variety of ways. Electrostatic passivation, utilizing like charges to repulse the nanocrystals, and steric passivation, using bulky molecules to physically keep the nanocrystal surfaces apart, are two examples of surface passivation methods.

Most typical nanocrystal synthetic methods, such as aerosol synthesis, pyrolysis, flame pyrolysis, laser pyrolysis, ball-milling, and laser ablation, produce nanocrystals which have no surface passivation of the types described herein. In fact, many of these methods produce nanocrystals that are clustered together as hard aggregates. Even if the synthesis does not result in aggregated nanocrystals, metal oxide nanocrystals without surface passivation tend toward aggregation because of inter-particle forces.

The liquid synthesis of metal oxide colloidal nanocrystals is a method of producing nanocrystals which are, at least partially, surface passivated during the synthesis. The liquid synthesis is performed in solvent with or without the presence of capping agents. The nanocrystals are protected against aggregation, at least partially, during the synthesis and afterwards, by capping agents. In cases where the synthesis is carried out in a coordinating solvent, the solvent molecules, or products thereof, may act as the capping agent to passivate the surface. After liquid synthesis, the nanocrystals are protected from forming aggregates by partial or total coverage of the nanocrystals with solvent(s), product(s) of the solvent(s), added capping agent(s), and/or combination thereof.

After synthesis of nanocrystals by liquid synthesis, the as-made surface passivation can be modified by a process known as a cap exchange or ligand exchange reaction in which one ligand or capping agent is at least partially replaced by a different one. In this process the nanocrystals are usually dispersed in a solvent along with the desired capping agent. In some instances the temperature of the suspension may be elevated to further drive the exchange process. As a result of the cap exchange, either the new capping agent is added to some fraction of the nanocrystal surface or a fraction of the previous surface passivation agents are replaced by the new capping agent, or some combination thereof. The new capping agent may be chosen in order to yield chemical compatibility between the effective nanocrystal surface and the solvent, or other media, chosen for the final dispersion or application.

As-synthesized nanocrystals, which have been produced by other methods and do not have surface passivation, can also be exposed to capping agents. While this also may result in some fraction of the surface of the nanocrystals being covered by the capping agents, this process may not be able to break apart any aggregates which will have formed previously, including both hard and soft aggregates. These aggregates of oxide nanocrystals are distinct from very weakly bound agglomerates of surface passivated nanocrystals where the passivation agents may create a porous spacer between the nanocrystals. In the weakly bound agglomerates, the inter-nanocrystal spacer layers provided by surface passivation are important because many of the surface to surface forces which cause aggregation are short range interactions, which can be reduced by the increased nanocrystal separation. However, in the absence of surface passivation, once the nanocrystal surfaces have been brought together, such as in the formation of hard aggregates, the short range forces dominate and it is difficult to separate the nanocrystals again.

Agglomerates of surface passivated nanocrystals, which can be broken up, may form during various points in the production of a dispersion, including during the washing of the particles, and the drying of powders. One of the advantages of using liquid synthesis to produce colloidal nanocrystals is that surface passivation of the as-synthesized nanocrystals can be used to prevent or reduce both hard and soft aggregates from forming during all stages of nanocrystal processing from the synthesis, to post-synthetic processing, to formation of the final high quality dispersion.

SUMMARY

In order to achieve higher quality nanocomposites, nanocrystal particle size should advantageously be less than 10 nm in at least one dimension, with preferably a very narrow particle size distribution, and further with specific particle shape (rod, spherical, etc). In addition, the surface chemistry of the nanocrystal is advantageously well passivated, preventing or reducing aggregation, and increasing or enhancing compatibility with the solvent(s) and/or the matrix material, and thereby allowing or enhancing dispersion of the nanocrystals into a nanocomposite or other substrate containing same.

Nanocrystals of the present disclosure will also be recognized in the art as including, for example, nanoparticles, quantum dots and colloidal particles and can include particles that are crystalline and/or amorphous with sizes ranging from a few hundred nanometers down to 1 nm or less. Due to their small size, nanocrystals can possess dramatically different physical properties compared to bulk forms of similar materials, due, for example, to the quantum effect and/or a greater area/volume ratio. Nanocrystals of the present disclosure may be useful in, for example, applications ranging from metallurgy to chemical sensors, and industries ranging from pharmaceuticals to paints and coatings to cosmetics. Microelectronic and optical applications are also contemplated.

Colloidal semiconductor nanocrystals are chemically synthesized, on the nanometer scale with ligands or capping agents on the surface of the nanocrystals to afford both dispersibility and stability in solution. In a basic chemical synthetic route, the precursors of the semiconductor nanocrystals react or decompose in the presence of a stabilizing organic capping agent or a solvent. Varying the size of the nanocrystals can be achieved by changing the reaction time or temperature profile, or adjusting the sequence of precursor addition, or varying the concentrations of chemical precursors, or varying the ratios of concentrations of chemical precursors, and/or varying the capping agents.

The chemistry of the capping agent effects and/or controls several of the system parameters in the manufacture of the nanocrystals and/or the nanocomposites, such as the growth rate, shape, and dispersibility of the nanocrystals in a variety of solvents and solids, and even the excited state lifetimes of charge carriers in the nanocrystals. The flexibility of the resulting effects of this chemical synthesis is demonstrated by the fact that often one capping agent is chosen for its growth control properties and is later substituted out, either partially or fully, after synthesis for a different capping agent. This substitution may be carried out for a variety of reasons, including, but not limited to: in order to provide a nanocrystal/media interface more suitable to the given application or to modify the optical properties of the nanocrystal.

Synthetic methods for producing colloidal semiconductor nanocrystals of zinc oxide (ZnO), yttrium oxide ($Y_2O_3$), hafnium oxide ($HfO_2$), and zirconium oxide ($ZrO_2$), hafnium-zirconium oxide [$HfO_2:ZrO_2$] and titanium-zirconium oxide [$TiO_2:ZrO_2$], as well as capping and cap-exchange of these nanocrystals and dispersion of these materials in solvents and polymers and the creation of nanocomposites are described herein.

Functionalized organosilanes are a common class of organic compounds used to populate the surface of a nanocrystalline oxide material as capping agents. These organosilanes are typically composed of head and tail components.

The head of a functionalized organosilane is typically either a trialkoxysilane group or a trichlorosilane group, although bi- and mono-substituted alkoxy and chloro silane are possible. The head anchors to the surface of the oxide through a covalent bond with the hydroxide groups (—OH) or —OR group wherein R is an alkyl or aryl group, present at the surface, eliminating an alcohol, alkyl chloride, water or HCl as a by-product. The tails of a functionalized organosilane can include one, or more of an alkyl chains of varying lengths, aryl groups, or ether groups, amines, thiols, or carboxylic acid.

FIG. 1 show an exemplary attachment of an organosilane to a nanocrystal surface through an alcohol elimination reaction. In this reaction, the nanocrystals with a polar surface containing —OH groups (101) react with an organosilane (102) to form the organosilane capped nanocrystals (103).

Other classes of organic compounds used as capping agents to passivate the surface of an oxide material include organocarboxylic acids and organoalcohols. The head of organocarboxylic acids is a carboxylic acid (—COON) group and organoalcohols is an —OH group. The head anchors to the surface of the oxide through a covalent bond with the hydroxide groups (—OH) or —OR (R=alkyl or aryl) group present at the surface, eliminating an alcohol, or water as a by-product. The tails of a functionalized organocarboxylic acids and organoalcohols can be composed of alkyl chains of a variety of lengths, aryl groups, ether groups, amines, thiols, or carboxylic acids.

The use of a capping agent such as functionalized organosilanes, alcohols or carboxylic acids on colloidal nanocrystals impart a number of desired characteristics, such as for example, controlling their compatibility to various dispersing solvents, such as polar or non-polar media, which can thereby reduce nanocrystal aggregation.

The present disclosure further includes methods for the surface modification of nanocrystals with organosilanes, organoalcohols and/or organocarboxylic acids. The method includes depositing capping agents during the synthesis of the nanocrystals or through ligand exchange of at least part of the capping agent originally present on the nanocrystal with a second one after the synthesis. These reactions can be performed under ambient, heated, and/or high temperature/high pressure conditions.

The present disclosure further includes a nanocomposite material containing a matrix and nanocrystals, which have been, for example, mixed, stirred, or dispersed therein. Nanocomposites according to the present disclosure may be fabricated by, for example, melt blending, in situ polymerization, and/or solvent mixing of the nanocrystals and the matrix materials or precursors of the matrix.

In melt blending, nanocrystals are mixed with a polymer in its molten state with the assistance of mechanical forces. In situ polymerization involves mixing nanocrystals with monomer(s) which are then polymerized to form a composite. Solvent mixing involves the use of solvent(s) to disperse both the nanocrystals and the polymer whereby uniform dispersion of the polymer and nanocrystals is achieved by removal of the solvent.

The present disclosure includes preparation methods for nanocomposite materials which include solvent mixing of polymers, or polymer precursors, with nanocrystals capped with a functionalized organosilanes, organoacids or organoalcohols; and in situ polymerization of capped nanocystals and monomers of polymers.

DETAILED DESCRIPTION

Figure 1:
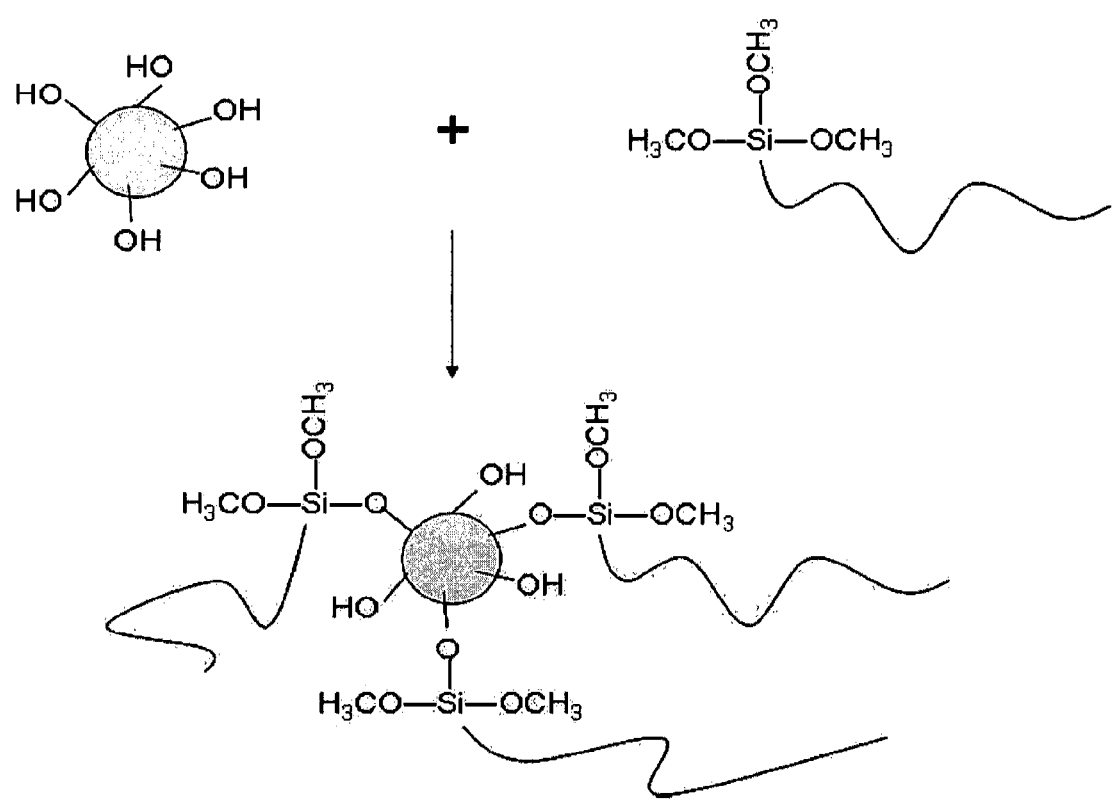
FIG. 1 illustrates the attachment of an organosilane to a nanocrystal surface through alcohol elimination.

The synthetic methods to prepare high quality semiconductor metal oxide nanocrystals described herein include synthetic methods wherein a precursor of the metal oxide is mixed or dissolved in at least one solvent and allowed to react for a certain period of time. The use of pressure or heating may be necessary in some cases.

At least in the case of $ZrO_2$ and $HfO_2$ nanocrystal syntheses, addition of water into the solvent surprisingly results in smaller particles than reactions carried out without addition of water, as described in the examples. By controlling the amount of water added to the solvent the average particle size of the nanocrystals can be controlled.

The precursors of the metal oxides may be one or more of alkoxides, such as: zirconium ethoxide ($Zr(OCH_2CH_3)_4$), zirconium n-propoxide ($Zr(OCH_2CH_2CH_3)_4$), zirconium isopropoxide ($Zr(OCH(CH_3)_2)_4$), zirconium n-butoxide ($Zr(OCH_2CH_2CH_2CH_3)_4$), zirconium t-butoxide ($Zr(OC(CH_3)_3)_4$), hafnium ethoxide ($Hf(OCH_2CH_3)_4$), hafnium n-propoxide ($Hf(OCH_2CH_2CH_3)_4$), hafnium isopropoxide ($Hf(OCH(CH_3)_2)_4$), hafnium butoxide ($Hf(OCH_2CH_2CH_2CH_3)_4$), hafnium t-butoxide ($Hf(OC(CH_3)_3)_4$), titanium ethoxide ($Ti(OCH_2CH_3)_4$), titanium n-propoxide ($Ti(OCH_2CH_2CH_3)_4$), titanium isopropoxide ($Ti(OCH(CH_3)_2)_4$), titanium t-butoxide ($Zr(OC(CH_3)_3)_4$), titanium n-butoxide ($Ti(OCH_2CH_2CH_2CH_3)_4$), zinc ethoxide ($Zn(OCH_2CH_3)_2$), zinc n-propoxide ($Zn(OCH_2CH_2CH_3)_2$), zinc isopropoxide ($Zr(OCH(CH_3)_2)_2$), zinc butoxide ($Zn(OCH_2CH_2CH_2CH_3)_2$); acetates or acetylacetonates, such as, zirconium acetate ($Zr(OOCCH_3)_4$), zirconium acetylacetonate ($Zr(CH_3COCHCOCH_3)_4$), zinc acetate ($Zn(OOCCH_3)_2$), zinc acetylacetonate ($Zn(CH_3COCHCOCH_3)_2$), hafnium acetate ($Hf(OOCCH_3)_4$); halides such as zirconium chloride ($ZrCl_4$), zirconium fluoride ($ZrF_4$), zirconium iodide ($ZrI_4$), zirconium bromide ($ZrBr_4$), hafnium bromide ($HfBr_4$), hafnium chloride ($HfCl_4$), hafnium iodide ($HfI_4$), titanium chloride ($TiCl_4$), titanium bromide ($TiBr_4$), titanium iodide (TiI$_4$), titanium fluoride (TiF$_4$), zinc chloride (ZnCl$_2$), zinc bromide (ZnBr$_2$), zinc iodide (ZnI$_2$), zinc fluoride (ZnF$_2$) or other organometallic compounds.

Solvents useful in the present disclosure include benzyl alcohol, phenol, oleyl alcohol, toluene, butanol, propanol, isopropanol, ethanol, water, propylene glycol monomethyl ether (PGME), propylene glycol methyl ether acetate (PG-MEA), ethyl lactate (EL), and 2-propoxy-propanol (PnP), acetone, tetrahydrofuran, cyclic ketones and mixtures thereof.

The surface of nanocrystals of the present disclosure are optionally capped with at least one capping agent such as organosilane, organoalcohol or organocarboxylic acid. Examples of organosilanes of the present disclosure include, n-propyltrimethoxysilane, n-propyltriethoxysilane, n-octyltrimethoxysilane, n-octyltriethoxysilane, phenylrimethoxysilane, 2-[methoxy(polyethyleneoxy)propyl]-trimethoxysilane, methoxy(triethyleneoxy)propyltrimethoxysilane, 3-aminopropyltrimethoxysilane, 3-mercaptopropyltrimethoxysilane, 3-(methacryloyloxy)propyl trimethoxysilane, 3-isocyanatopropyltriethoxysilane, 3-isocyanatopropyltrimethoxysilane, and glycidoxypropyltrimethoxysilane.

Examples of organoalcohols of the present disclosure include, heptanol, hexanol, octanol, benzyl alcohol, phenol, ethanol, propanol, butanol, oleylalcohol, dodecylalcohol, octadecanol and triethylene glycol monomethyl ether.

Examples of organocarboxylic acids of the present disclosure include, octanoic acid, acetic acid, propionic acid, 2-[2-(2-methoxyethoxy)ethoxy]acetic acid, oleic acid, benzoic acid.

Capped colloidal semiconductor nanocrystals of the present disclosure are, optionally, removed from and re-dispersed into solvents, such as, water, tetrahydrofuran, ethanol, methanol, acetonitrile, PGMEA, PGPE, PGME, cyclic ketones, ethyl lactate, acetone, naphtha, hexane, heptane, toluene or a mixture thereof.

Semiconductor nanocrystals can be added into a matrix to form a nanocomposite. The matrix material of the present disclosure include, poly(acrylonitrile-butadiene-styrene) (ABS), poly(methyl methacrylate) (PMMA), celluloid, cellulose acetate, poly(ethylene-vinyl acetate) (EVA), poly(ethylene vinyl alcohol) (EVOH), fluoroplastics, polyacrylates (Acrylic), polyacrylonitrile (PAN), polyamide (PA or Nylon), polyamide-imide (PAI), polyaryletherketone (PAEK), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyketone (PK), polyester, polyethylene (PE), polyetheretherketone (PEEK), polyetherketoneketone (PEKK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polytrimethylene terephthalate (PTT), polyurethane (PU), polyvinyl acetate (PVA), polyvinyl chloride (PVC), polyvinylidene chloride (PVDC), poly(styrene-acrylonitrile) (SAN); a spin-on-glass (SOG) polymer, such as: Siloxane-spin-on polymers in Ethanol, Propylene Glycol Methyl Ether Acetate (PGMEA), isopropyl alcohol or mixture of these solvents, JSR Micro topcoat (NFC TCX 014 in 4-methyl-2-pentanol), JSR Micro photoresist (ARF 1682J-19), and silicones, such as: Polydimethylsiloxane (PDMS) and polymethylphenylsiloxane.

Examples of nanocrystals include, but are not limited to, CuCl, CuBr, CuI, AgCl, AgBr, AgI, Ag$_2$S, Ag$_2$Te, Al$_2$O$_3$, Ga$_2$O$_3$, In$_2$O$_3$, FeO, Fe$_2$O$_3$, Fe$_3$O$_4$, TiO$_2$, MgO, Eu$_2$O$_3$, CrO$_2$, CaO, MgO, ZnO, Mg$_x$Zn$_{1-x}$O, SiO$_2$, Cu$_2$O, Zr$_2$O$_3$, ZrO$_2$, SnO$_2$, ZnS, HgS, Fe$_2$S, Cu$_2$S, CuIn$_2$S$_2$, MoS$_2$, In$_2$S$_3$, Bi$_2$S$_3$, GaP, GaAs, GaSb, InP, InAs, In$_x$Ga$_{1-x}$As, SiC, Si$_{1-x}$Ge$_x$, CaF$_2$, YF$_3$, YSi$_2$, GaInP$_2$, Cd$_3$P$_2$, CuIn$_2$Se$_2$, In$_2$Se$_3$, HgI$_2$, PbI$_2$, ZnSe, CdS, CdSe, CdTe, HgTe, CdHgTe, PbS, BN, AlN, GaN, InN, Al$_x$Ga$_{1-x}$N, Si$_3$N$_4$, ZrN, Y$_2$O$_3$, HfO$_2$, Sc$_2$O$_3$, and their mixtures or alloys, wherein x may have a value of between 0.01 to 0.99.

The present disclosure provides a method of making nanocrystals including dissolving precursors of said nanocrystals in at least one solvent to produce a solution, optionally at least one of heating and increasing pressure of said solution, and reacting the precursors or the precursors and the at least one solvent of the solution to form the nanocrystals.

The nanocrystals may be capped with at least one agent to increase the solubility or dispersibility of the nanocrystals in at least one solvent or other media, or some combination of solvent and other media.

In the method of the disclosure, nanocrystals may be capped with at least one agent which may include at least one organosilane, organoalcohol or organocarboxylic acid. These capping agents may impart uniform dispersion of the nanocrystals in different media such as hydrophobic or hydrophilic media by creating an effective nanocrystal surface which is formed by the full or partial shell of capping agents whose tail groups have a polarity compatible with the media.

The capping method of the present disclosure may including capping of the nanocrystals with the at least one capping agent in the solution, prior to, during, or after said reacting the precursors. The methods of the present disclosure further include purifying and/or separating the nanocrystals prior to, or after, the capping method of the present disclosure.

Figure 2:
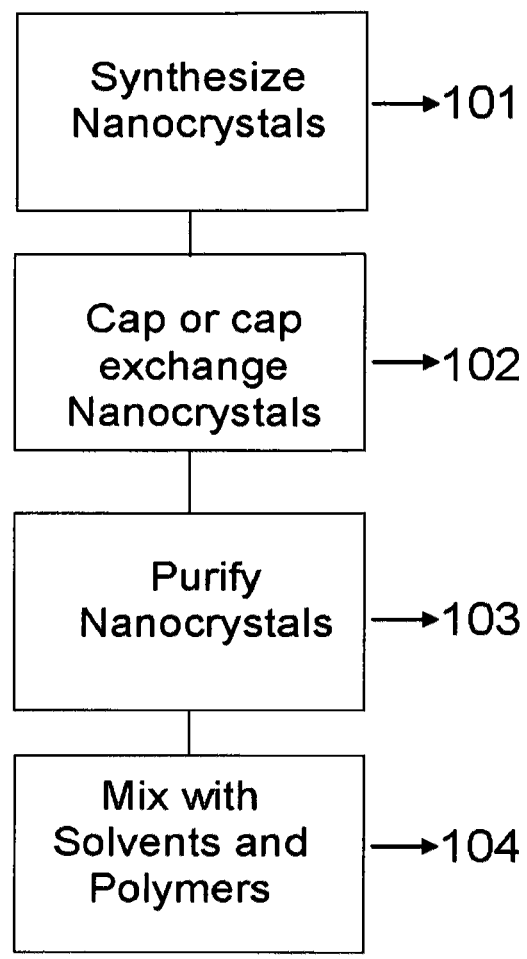
FIG. 2 shows, in a block diagram, process steps of the present disclosure for the formation of a nanocomposite material described herein.

The method of the disclosure includes capping the as-synthesized, purified, and/or separated nanocrystals with at least one capping agent to produce at least partially capped nanocrystals. The at least partially purified capped nanocrystals may be further purified and/or separated according to methods of the present disclosure. Nanocrystals and capped nanocrystals may be dispersed in a material, including solvent, polymer, or some combination thereof in methods of the present disclosure. FIG. 2 is a block diagram exemplifying formation of a colloidal suspension. In the exemplified method, nanocrystals are synthesized (101), capped or cap exchanged with at least one capping agent (102), purified (103) and mixed with solvents or polymer solutions (104).

The present disclosure further includes methods of exchanging, fully or partially, the pre-existing organic moieties or other capping agents present on the nanocrystal surface resulting from the synthesis of the nanocrystals or other previous cap exchange reactions with functionalized organosilanes, organoalcohols and organocarboxylic acids in a cap exchange reaction.

Functionalized capping agents are covalently bonded to colloidal semiconductor nanocrystals according to an aspect of the present disclosure during synthesis of the colloidal semiconductor nanocrystal.

Functionalized capping agents are optionally covalently bonded to semiconductors in the present disclosure by removing pre-existing organic moieties from the surface of semiconductor nanocrystals with an acid and then covalently bonding the functionalized capping agents to the surface of the semiconductor nanocrystals. Examples of acids to remove pre-existing organic moieties include, for example, strong acids (e.g., HCl, HNO$_3$, and/or H$_2$SO$_4$), weak acids (e.g., H$_3$PO$_4$), and/or organic acids (e.g., acetic acid).

Alternatively, nanocrystals are functionalized with capping agents without forming covalent bonds.

The present disclosure includes nanocrystals and at least partially capped nanocrystals made by methods described herein.

Methods of the present disclosure further includes methods of forming a film or coating including dispersing the nanocrystals or at least partially capped nanocrystals of the present disclosure in a further material to form a dispersion, and applying the dispersion to a surface. The applying methods may include spin coating, spraying, dipping, screen printing, rolling, painting, printing, ink jet printing, depositing by evaporation and/or vapor deposition.

Figure 3:
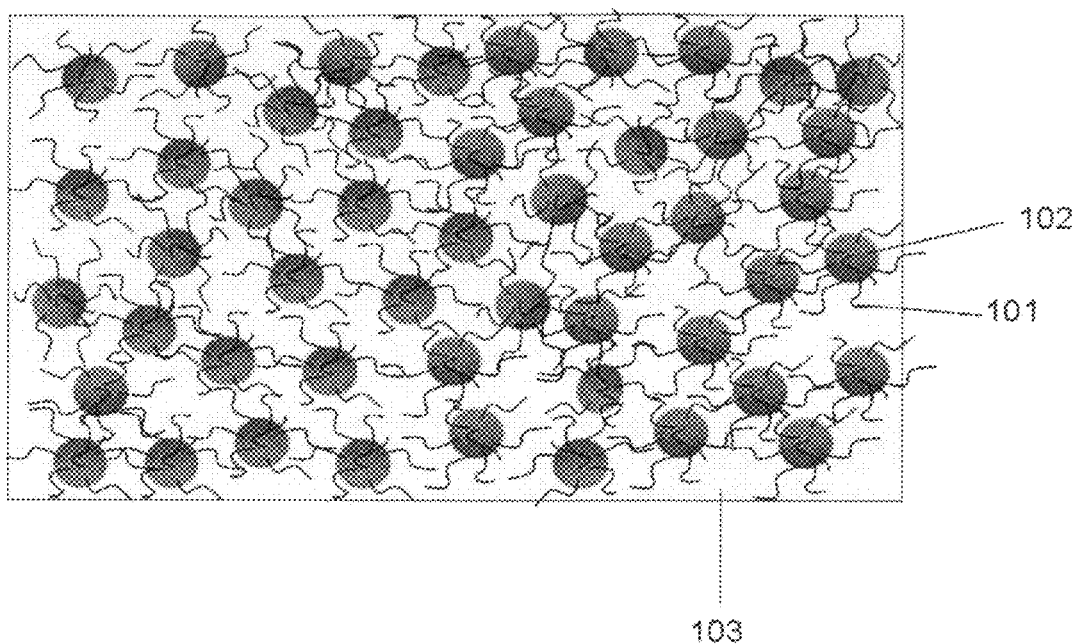
FIG. 3 exemplifies a silane capped colloidal semiconductor nanocrystals in a polymeric film.

Methods of the present disclosure include forming a nanocomposite which includes combining the nanocrystals or the at least partially capped nanocrystals of the present disclosure with a further material and forming the nanocomposite. FIG. 3 is an exemplary picture of nanocrystals (102) capped with a capping agent (101) dispersed in a polymer matrix (103).

Methods of the present disclosure include forming a nanocomposite by, for example, curing, polymerization, laminating, extrusion, injection molding, mold casting, spin coating, dip coating, brushing, spraying, and/or printing.

The present disclosure further includes methods of forming homogeneous mixtures of the components of a nanocomposite with a variety of different methods, before assembling the components into the final composite material suitable for desired applications.

The nanocrystals or at least partially capped nanocrystals of the present disclosure may be formed from zinc oxide, hafnium oxide, zirconium oxide, titanium-zirconium oxide, hafnium-zirconium oxide, yttrium oxide or other semiconductor material.

The products and methods of the present disclosure are exemplified by the following non-limiting examples.

Example 1

Synthesis and Capping of Nanocrystals

Synthesis of Zirconium Oxide ($ZrO_2$) Nanocrystals

Zirconium oxide nanocrystals having a size in the range of 1-10 nm can be prepared from precursors such as Zirconium (IV) n-butoxide, zirconium n-propoxide, Zirconium isopropoxide isopropanol or zirconium ethoxide. Zirconium n-butoxide or zirconium n-propoxide would be advantageously used as precursors depending on final product desired.

In an exemplary method, a zirconium alkoxide precursor, such as, but not limited to, Zirconium n-butoxide, zirconium n-propoxide, zirconium isopropoxide isopropanol or zirconium ethoxide, is mixed with a solvent or mixture of solvents, including benzyl alcohol, phenol, oleyl alcohol, butanol, propanol, isopropanol, water, tetrahydrofuran, ethanol, methanol, acetonitrile, toluene, PGMEA, PGPE, PGME, 2-methyl-1-propanol, or triethylene glycol monomethyl ether and sealed within an autoclave. The reaction mixture is heated to a temperature between 250-350° C. Once the reaction mixture reaches the set temperature, the temperature is maintained for a length of time ranging from 20 minutes to 24 hours depending in part on the solvent or solvent mixtures and/or the temperature of the reaction. As-synthesized zirconium oxide nanocrystals are collected as a white milky suspension.

In a further example, zirconium oxide nanocrystals were produced from a mixture of 30 millimoles of zirconium isopropoxide isopropanol or zirconium ethoxide and 300 milliliters of benzyl alcohol in an inert atmosphere which was sealed within an autoclave. The reaction mixture was heated to 350° C. at a heating rate is 10° C./min. Once the reaction mixture reached 350° C., the temperature was maintained for 20-60 min. A white milky solution of as-synthesized $ZrO_2$ nanocrystals was collected after the autoclave was cooled down to the room temperature.

In a further example, zirconium oxide nanocrystals were prepared from 45 millimoles of zirconium isopropoxide isopropanol or zirconium ethoxide mixed with 300 milliliters of benzyl alcohol in an inert atmosphere which was transferred to an autoclave. The reaction mixture was heated to 300-350° C. for 1-2 hours at a heating rate of 10° C./min. The pressure of the reaction reaches 100 to 500 psi. After the reaction was complete and the reactor was returned to room temperature, a white milky solution of as-synthesized zirconium oxide nanocrystals was collected.

An exemplary synthetic method using zirconium n-butoxide as the precursor is as follows: 21.58 g of 80% (w/w) Zirconium (IV) n-butoxide in 1-butanol solution (containing 17.26 g or 45 mmol Zirconium (IV) n-butoxide) was mixed with 300 ml of benzyl alcohol in a glove box and then transferred into an autoclave with a glass liner. The setup was sealed under an argon atmosphere to prevent oxygen and moisture contamination. The autoclave was then heated up to 325° C., kept at this temperature for one hour and then cooled down to room temperature. A white milky solution of as-synthesized zirconium oxide nanocrystals was collected.

Figure 4:
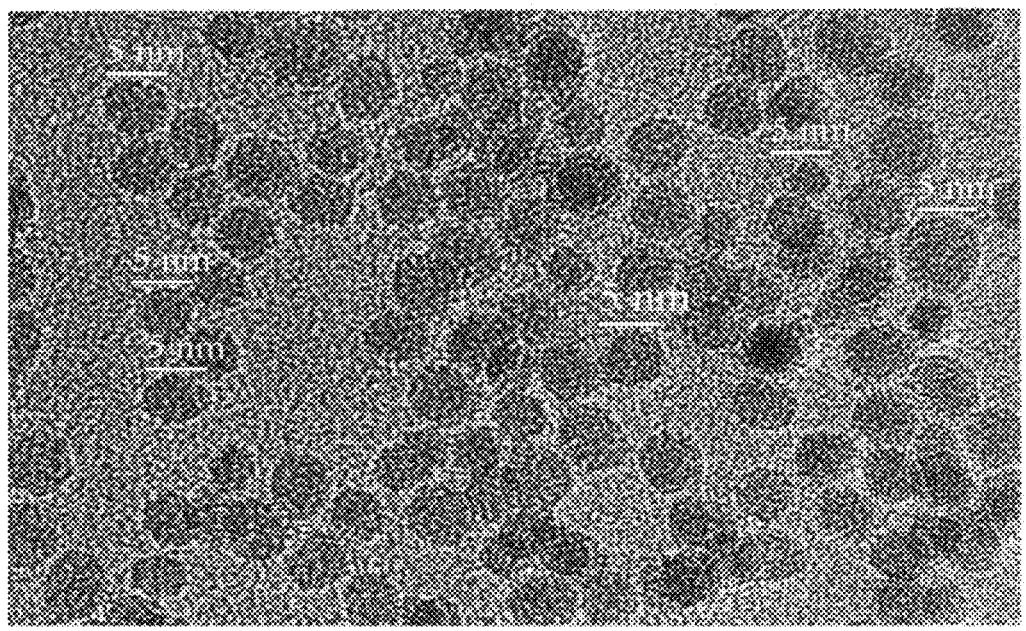
FIG. 4 shows the TEM image of nanocrystals synthesized from zirconium butoxide.

Zirconium n-butoxide is received as a solution in 1-butanol (80% w/w). 1-butanol can be removed from the precursor before the synthesis under vacuum and/or heating (30-50° C.), during the synthesis by releasing the pressure of the autoclave when the temperature reaches around 100° C. or after the reaction is completed. FIG. 4 is the TEM image of the nanocrystals obtained from the reaction without removing 1-butanol. The nanocrystals are spherical in shape and around 5 nm in diameter.

An exemplary synthetic method using zirconium n-propoxide as the precursor is as follows: 21.06 g of 70% (w/w) Zirconium (IV) n-propoxide in 1-propanol solution (containing 14.74 g or 45 mmol Zirconium (IV) n-propoxide) was mixed with 300 ml of benzyl alcohol in a glove box and then transferred into an autoclave. The setup was sealed under Argon atmosphere to prevent oxygen and moisture contamination. The autoclave was then heated up to 325° C., kept at this temperature for one hour and then cooled down to room temperature. A white milky solution of as-synthesized zirconium oxide nanocrystals was collected.

Figure 5:
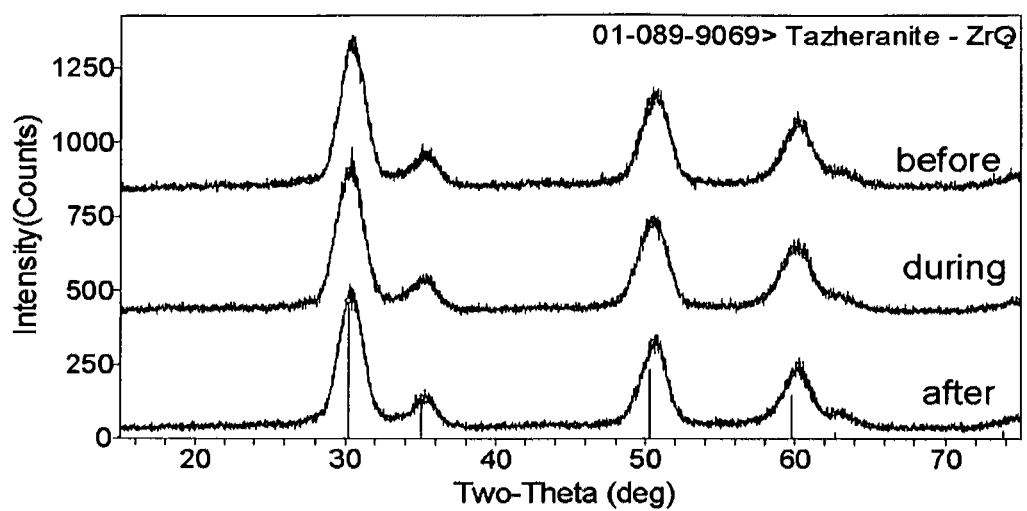
FIG. 5 shows the XRD patterns of $ZrO_2$ nanocrystals synthesized from zirconium propoxide by removing 1-propanol before, during or after the reaction.
Figure 6:
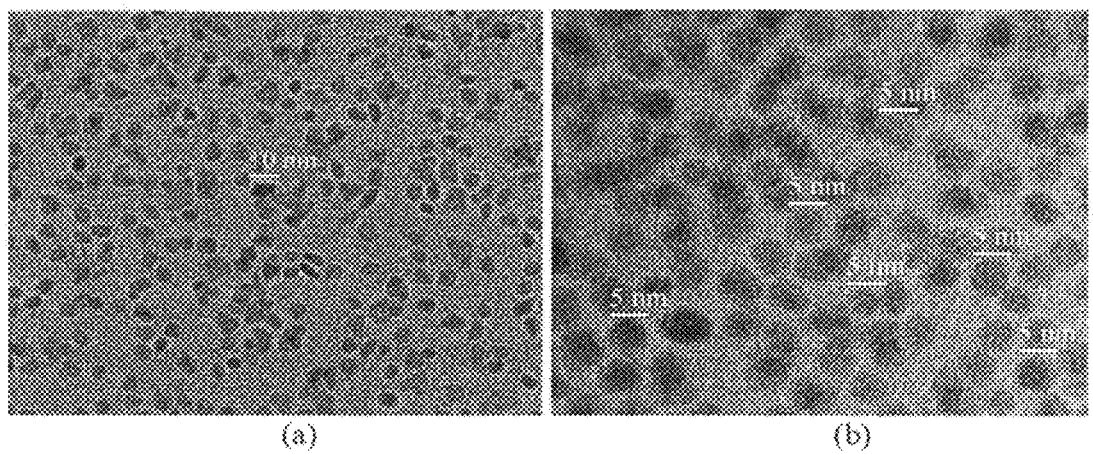
FIG. 6 shows the TEM images of $ZrO_2$ nanocrystals synthesized from zirconium propoxide by removing 1-propanol a) before, and b) after the reaction.

Zirconium n-propoxide is received as a solution in 1-propanol (70% w/w). 1-propanol can be removed from the precursor before the synthesis under vacuum and/or upon heating (30-60° C.). It can also be removed during the synthesis by releasing the pressure of the autoclave when the temperature reaches around 100° C. or it can be removed after the synthesis. The nanocrystals obtained from the reactions where 1-propanol was removed from the precursor before, during or after the reaction result in around 5 nm $ZrO_2$ nanocrystals. These nanocrystals have the same crystal structure as shown by the respective XRD patterns of the nanocrystals shown in FIG. 5. The nanocrystals obtained by removal of 1-propanol before or during the reaction are more spherical and monodisperse based on a comparison of the TEM images shown in FIG. 6a for the nanocrystals obtained with removal before the reaction and FIG. 6b without removal of 1-propanol.

To increase the yield of the reaction without affecting the nanocrystal quality the concentration of the precursor, such as zirconium isopropoxide isopropanol, zirconium etoxide, zirconium n-propoxide or zirconium n-butoxide, can be increased 5-20 times without changing the amount of the solvent used.

$ZrO_2$ nanocrystals can be synthesized in a variety of solvents and solvent mixtures. A change in the solvent used in the synthetic method can lead to a change in the surface properties of the nanocrystals and, in some cases, can cap the nanocrystals well enough that further surface modification in order to obtain dispersions with minimal scattering may be unnecessary. A list of alternative solvents includes, but is not limited to: 1-hexanol, oleyl alcohol, oleylamine, trioctylamine, and methyl triethylene glycol. A list of alternative solvent mixtures includes, but is not limited to: mixtures of benzyl alcohol with 1-hexanol, oleyl alcohol, triethylene glycol monomethyl ether and trioctylamine.

$ZrO_2$ may also be synthesized in a different manner in order to prepare nanocrystals with a hydrophobic surface chemistry. This may be useful for applications which benefit from the use of hydrophobic solvents to create dispersions of nanocrystals. An example of the synthetic method to produce $ZrO_2$ nanocrystals with hydrophobic surface is as follows: the solvent for the $ZrO_2$ nanocrystals synthesis contains a mixture of oleyl alcohol and benzyl alcohol with different volume ratios. The volume ratio of oleyl to benzyl alcohol in which the reaction is run may be chosen from the following non-limiting list of ratios: 1:3, 1:1, or pure oleyl alcohol. In a typical reaction, 3 millimole of zirconium isopropoxide isopropanol is added to a 20 ml mixture containing 10 ml anhydrous benzyl alcohol and 10 ml oleyl alcohol in an inert atmosphere. The mixture is stirred for approximately one hour. The reaction mixture is then added to an autoclave reactor under an inert atmosphere. Then the reactor is heated to 325° C. and maintained at 325° C. for 1 hour with stirring. After cooling the nanocrystals are precipitated out of the solution with ethanol.

The exemplary synthetic methods described herein are carried out in an autoclave at temperatures which may be higher than the boiling point of some of the solvents used. This can generate pressures in the 100-900 psi range, typically around 250 psi. To eliminate the high pressures which may normally be present in the $ZrO_2$ nanocrystals synthesis, a solvent or a mixture of solvents with higher boiling points may be used. One, non-limiting, example of a higher boiling point solvent is Dowtherm MX, a mixture of alkylated aromatics, from Dow Chemicals. Dowtherm MX can be used alone or in combination with other solvents such as benzyl alcohol. When used alone for the $ZrO_2$ nanocrystal synthesis, the pressure in the autoclave reactor is less than 100 psi, and typically less than 20 psi.

A typical example of a $ZrO_2$ nanocrystal synthesis carried out in a mixture of benzyl alcohol and Dowtherm MX is as follows: 100 ml of Dowtherm MX, 8.13 millimoles of Zirconium Isopropoxide isopropanol and 30 ml of Anhydrous Benzyl Alcohol are mixed in a 250 ml flask for 30 min with magnetic stirrer at 500 rpm in a glove box. The mixture is then loaded in to a 600 ml glass-lined Parr autoclave reactor. The reactor was then sealed in the glove box. The reaction mixture is heated to 325° C. at heating rate of 10° C./min while stirring and kept at this temperature for 1 hour with stirring. After that it was cooled to room temperature and a milky white suspension of $ZrO_2$ nanocrystals is obtained.

A typical example of the procedure for a $ZrO_2$ nanocrystal synthesis using only Dowtherm MX as the solvent follows: 100 ml of Dowtherm MX is mixed with 3.15 g of Zirconium Isopropoxide isopropanol in a 250 ml flask for 30 min at 500 rpm with magnetic stirrer in a glove box. The mixture is then loaded in to a 600 ml glass-lined Parr Reactor. The reactor was then sealed while in the glove box, before being transferred out for the reaction. The reaction mixture is heated to 325° C. at heating rate of 10° C./Min min with stirring and kept at this temperature for 1 hour with stirring. After that it was cooled to room temperature and a milky white suspension of $ZrO_2$ nanocrystals is obtained.

Alternatively, precursors other than zirconium (IV) isopropoxide isopropanol may be used to synthesize $ZrO_2$ nanocrystals in solvents with a higher boiling point than the reaction temperature, or a mixture of these solvents with benzyl alcohol. These alternative precursors may include but are not limited to zirconium (IV) ethoxide, zirconium (IV) n-propoxide, and zirconium (IV) n-butoxide.

Figure 7:
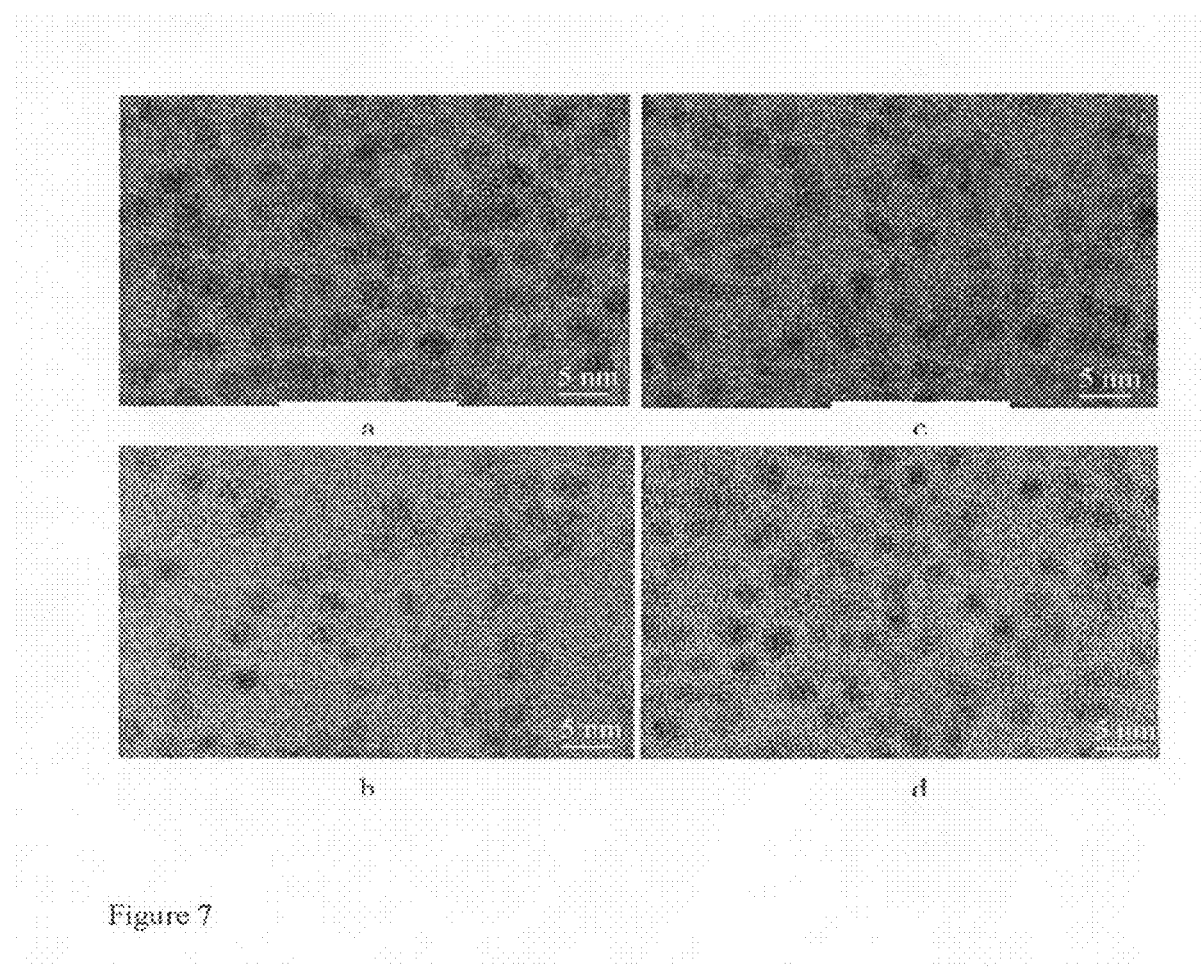
FIG. 7 shows TEM images of $ZrO_2$ nanocrystals with different sizes

Synthesis of 1-5 nm $ZrO_2$ Nanocrystals $ZrO_2$ nanocrystals can be synthesized with average diameters from 1 to 5 nm, preferably 1 to 3 nm, by controlling the amount of water in the reaction mixture during the solvothermal synthesis. These smaller sized nanocrystals (1-5 nm) may be desirable for increased specific surface area with respect to larger (6-10 nm) nanocrystals or for use in applications where the smaller physical size may be beneficial. A typical example of the experimental protocol for the synthesis of these nanocrystals is as follows: In a vial, 30 ml of benzyl alcohol and 0.08 ml of water (4.44 mmol) were stirred for 1 hour and transferred into the glovebox. In the glovebox, 4.49 millimoles of zirconium (IV) isopropoxide isopropanol ($Zr(OPr^i)_4$ $(HOPr^i)$)-, (~1:1 water to precursor ratio) was stirred with the benzyl alcohol solution for 4 hours. The precursor was completely dissolved into the solvent and a clear solution was obtained. The reaction mixture was then transferred to an autoclave and sealed within the vessel. The reaction mixture was then heated at 325° C. for 1 hour (15 minutes ramp up to 250° C., 3 minutes ramp up to 265° C., 3 minutes ramp up to 280° C., 3 minutes ramp up to 295° C., 3 minutes ramp up to 310° C., 3 minutes ramp up to 325° C.) while stirring. After cooling to room temperature, a white slurry and a faint yellow solution were obtained. The XRD pattern of the solid matches that of $ZrO_2$ and the TEM images of the nanocrystals shows that the particle size is around 3 nm. FIGS. 7a, b, c, and d show the TEM images of the nanocrystals obtained from 1:1, 1:2, 1:3 and 1:4 molar ratio of precursor to water in the reaction mixture, respectively. FIG. 7 shows that as the ratio of water to precursor increased the particle size gets even smaller with 1:4 water to precursor ratio resulting in the smallest average particle size (~2 nm) among the exemplary ratios of 1:1, 1:2, 1:3 and 1:4.

Alternatively $ZrO_2$ nanocrystals may be synthesized with average diameters from 1 to 5 nm, preferably 1 to 3 nm, using precursors other than zirconium (IV) isopropoxide isopropanol. These alternative precursors may include zirconium (IV) ethoxide, zirconium (IV) n-propoxide, and zirconium (IV) n-butoxide.

The heating temperature and time of the exemplary synthetic routes described herein for the synthesis of $ZrO_2$ nanocrystals can be adjusted such that the reaction temperature can be varied from 250-350° C. while the reaction time can be varied from 20 min-24 hours. Reactions carried out at the lower end of the temperature range may require longer heating times and the reactions carried out at the higher end of this temperature range may require shorter times for a complete synthesis.

Synthesis of Titanium-Zirconium Oxide ($TiO_2$—$ZrO_2$) Nanocrystals

Metal-oxide nanocrystals containing both zirconium and titanium atoms can be synthesized by a modification of the synthetic route for $ZrO_2$ nanocrystals. These $TiO_2$—$ZrO_2$ metal oxide nanocrystals may be used in a variety of applications which call for the mixture of chemical properties, physical properties, or optical properties (or some combination therein) of $ZrO_2$ and $TiO_2$. One set of non-limiting examples of this $TiO_2$—$ZrO_2$ synthesis involves replacing the zirconium precursor with a mixture containing both a titanium precursor and a zirconium precursor in benzyl alcohol. Nanocrystals with different Ti/Zr atomic ratios can be made by adjusting the titanium and zirconium precursor concentrations with respect to each other while holding the total metal precursor concentration constant. $TiO_2$—$ZrO_2$ nanocrystals can be synthesized in this manner with the Ti:Zr ratio taking a value from the following non-limiting list: 1:3, 1:2, and 1:1.

A typical procedure for the synthesis of $TiO_2$—$ZrO_2$ nanocrystals with 1:1 Ti:Zr ratio is as follows: 15 mmol of zirconium isopropoxide isopropanol and 15 mmol of titanium isopropoxide were dissolved in 30 ml anhydrous benzyl alcohol under an inert atmosphere. The reaction mixture was then added to an autoclave reactor under an inert atmosphere. The reactor was heated to 300° C. and maintained at 300° C. for 1 hour with stirring. The resulting nanocrystals were precipitated out of solution with ethanol. The $TiO_2$—$ZrO_2$ nanocrystals have a size of around 5 nm based on TEM images. The elemental analysis results confirmed that the Ti/Zr atomic ratio in the sample was generally consistent with the atomic ratio of the two precursors.

A typical procedure for the synthesis of $TiO_2$—$ZrO_2$ nanocrystals with a Ti:Zr ratio of 1:2 involves the following: 20 mmol of zirconium isopropoxide isopropanol and 10 mmol of titanium isopropoxide were dissolved in 30 ml anhydrous benzyl alcohol under an inert atmosphere. The reaction mixture was then added to an autoclave reactor under an inert atmosphere. The reactor was heated to 300° C. and maintained at 300° C. for 1 hour with stirring. The resulting nanocrystals were precipitated out of solution with ethanol.

Alternatively the synthesis of $TiO_2$—$ZrO_2$ nanocrystals with various values of x may be synthesized using a mixture of titanium and zirconium which is not a mixture of zirconium isopropoxide isopropanol and titanium isopropoxide. The mixture of zirconium and titanium precursors may include a zirconium precursor from a non-limiting list including: zirconium ethoxide, zirconium n-propoxide, and zirconium n-butoxide, and a titanium precursor including titanium ethoxide, titanium n-propoxide, and titanium n-butoxide.

Synthesis of Hafnium-Zirconium Oxide ($HfO_2$—$ZrO_2$) Nanocrystals

Metal-oxide nanocrystals containing both zirconium and hafnium atoms in a single nanocrystal can be synthesized. $HfO_2$—$ZrO_2$ oxide nanocrystals with an 1:1 atomic ratio of hafnium to zirconium can be produced in an inert atmosphere by mixing 2 millimoles of hafnium isopropoxide isopropanol and 2 millimoles of zirconium chloride with 10 grams of trioctylphosphine oxide. The reaction mixture is then heated to 100° C., at a heating rate of 10° C./min, with vigorous stirring under an inert atmosphere. After 1 hour stirring at 100° C., trioctylphosphine oxide is melted and the hafnium and zirconium precursors are dissolved in melted trioctylphosphine oxide. The solution is then rapidly heated to 350° C., at a heating rate of 10° C./min, and kept at 350° C. for two hours. A white powder appeared and the solution became milky. After two hours, the reaction mixture is allowed to cool. When the reaction mixture reached 70° C., acetone is added, causing the nanocrystals to precipitate. The resulting hafnium-zirconium oxide nanomaterial is rod-like in shape (i.e., "nanorods").

In a further example, hafnium-zirconium oxide nanocrystals, may be prepared with a range of values for the hafnium to zirconium atomic ratio. For example, nanocrystals with a Hf:Zr ratio of 1:4 can be prepared with the following: 0.8 mmol of hafnium isopropoxide isopropanol, 1.2 mmol of zirconium isopropoxide isopropanol, 2 mmol of zirconium chloride, and 10 grams of trioctylphosphine oxide are mixed together in an inert atmosphere. The feeding sequence is arbitrary. The reaction mixture is heated to 100° C., at a heating rate of 10° C./min, with vigorous stirring under an inert atmosphere. The solution is then rapidly heated to 350° C., at a heating rate 10° C./min, and kept at 350° C. for two hours. A white powder forms and the solution becomes milky. After two hours, the reaction mixture is allowed to cool. When the reaction mixture reached 70° C., acetone is added, causing the $HfO_2$—$ZrO_2$ nanocrystals to precipitate. The precipitate is collected by centrifugation and the supernatant is decanted and discarded. The redispersion-precipitation procedure is repeated 4 times. The shape of hafnium zirconium oxide nanomaterials range from spheres to rod-like (i.e., "nanorods").

Synthesis of Hafnium Oxide ($HfO_2$) Nanocrystals

Figure 8:
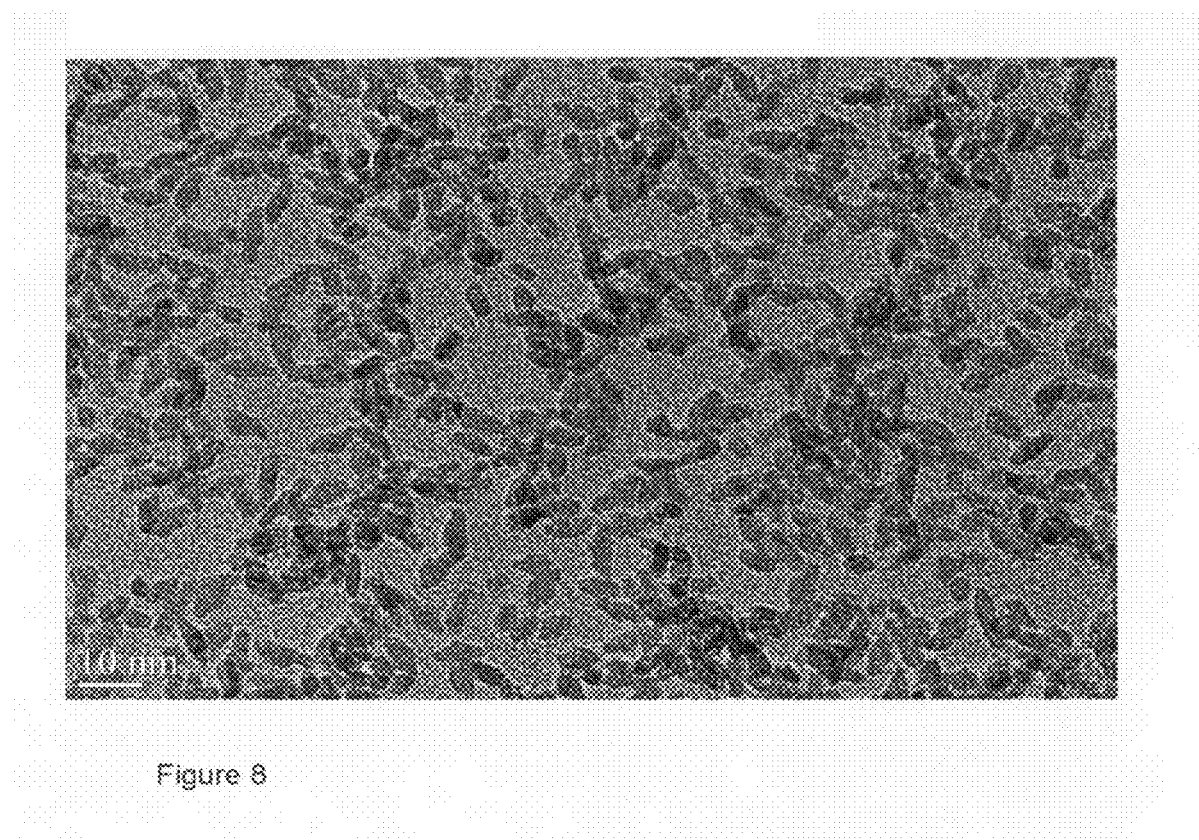
FIG. 8 shows the TEM image of the as-synthesized $HfO_2$ nanocrystals with rice-like morphology.

Hafnium oxide nanocrystals having a size in the range of 1-10 nm are synthesized in an inert atmosphere using a solvothermal synthetic method. An example of the synthetic method is as follows: a sample of hafnium alkoxide precursor, such as, but not limited to, hafnium isopropoxide isopropanol, or hafnium ethoxide, was mixed with an organic alcohol, such as, but not limited to, benzyl alcohol or 2-methyl-1-propanol, and sealed within an autoclave. The reaction mixture was heated to 250-350° C. Once the reaction mixture reached the set temperature, the temperature was maintained for a set time which can range from 20 minutes to 24 hours. As-synthesized hafnium oxide nanocrystals were collected as a white milky suspension. FIG. 8 shows a TEM image of the as synthesized $HfO_2$ nanocrystals which have a rice shape and are less than 10 nm in size.

A method of producing 6 g of hafnium oxide nanocrystals of the present disclosure includes mixing, in an inert atmosphere, a sample of 30 millimoles of hafnium ethoxide or hafnium isopropoxide isopropanol with 300 milliliters of benzyl alcohol which is then transferred to an autoclave. The reaction mixture is heated at 300-350° C. for 1-2 hours, with a heating ramp rate of 10° C./min. During reaction the pressure in the autoclave is less than 500 psi (~35 atmospheres). After the reaction time has elapsed and the reactor is returned to room temperature, a white milky solution of as-synthesized hafnium oxide nanocrystals is collected.

Alternatively, precursors other than hafnium (IV) isopropoxide isopropanol or hafnium ethoxide, may be used to synthesize $HfO_2$ nanocrystals in solvents with a higher boiling point than the reaction temperature, or a mixture of these solvents with benzyl alcohol. These alternative precursors may include but are not limited to hafnium (IV) n-propoxide, and hafnium (IV) n-butoxide.

Figure 9:
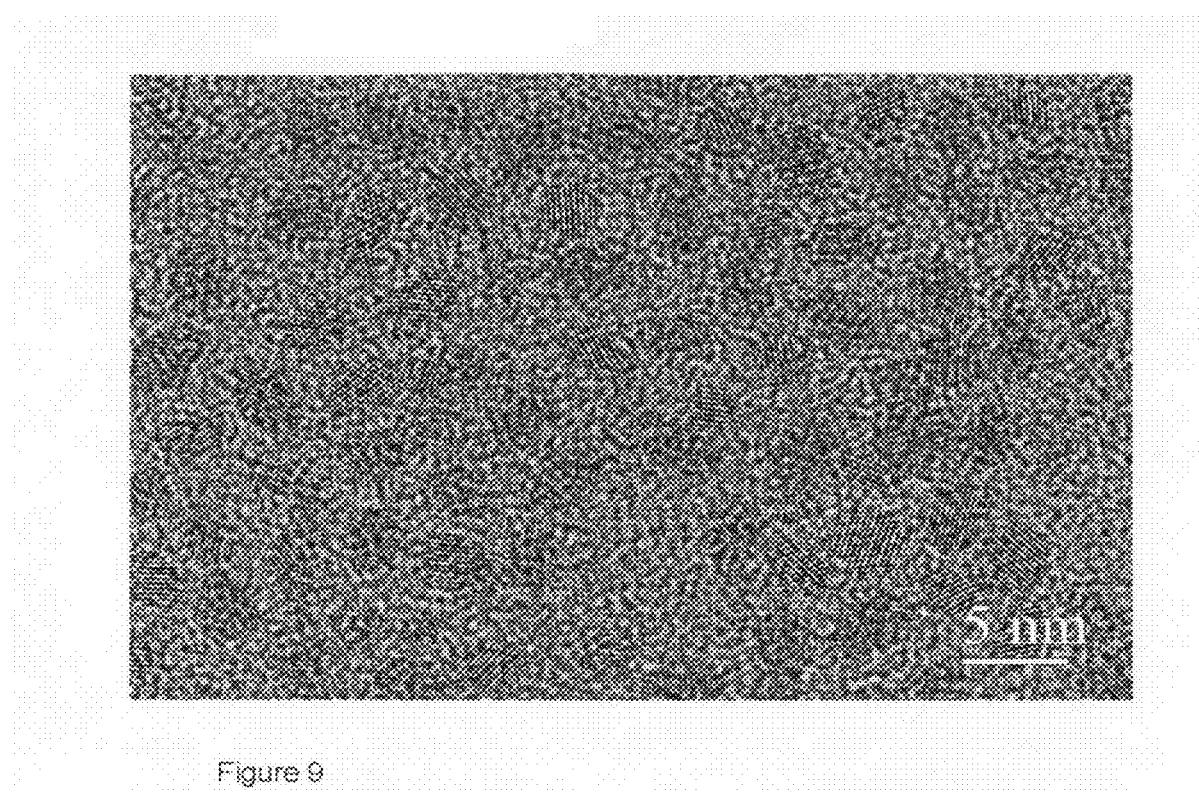
FIG. 9 shows a TEM image of the 2-5 nm $HfO_2$ nanocrystal.

Synthesis of 1-5 nm $HfO_2$ Nanocrystals $HfO_2$ nanocrystals can be synthesized with diameters of 1-5 nm, preferably 1-3 nm, by controlling the amount of water in the reaction mixture during the solvothermal synthesis. These smaller sized nanocrystals may be desirable for their increased specific surface area with respect to larger nanocrystals or for use in applications where the smaller physical size may be beneficial. A typical example of the experimental protocol for the addition of water in order to produce hafnium oxide nanocrystals in the 1-5 nm size range follows: 30 ml of benzyl alcohol and 0.1 ml of water are stirred for 3 hours in a vial which is then transferred into the drybox. In the drybox, 4.45 millimole of $Hf(OPr^i)_4(HOPr^i)$ (2.113 g) is stirred in the water/benzyl alcohol solution overnight with 1:1 water to hafnium isopropoxide molar ratio. The precursor completely dissolves into the solvent mixture. The reaction mixture is transferred to an autoclave and sealed within the vessel. The reaction mixture is then heated to 325° C., using a heating mantle, for 1 hour with stirring. After cooling to room temperature, a white slurry with a faint yellow solution are obtained. FIG. 9 shows the TEM images of the nanocrystal which are 2-5 nm in size.

Alternatively, $HfO_2$ nanocrystals may be synthesized with diameters of 1-5 nm, preferably 1-3 nm, starting from precursors other than hafnium isopropoxide isopropanol. These alternative precursors may include but are not limited to hafnium ethoxide, hafnium n-propoxide, and hafnium n-butoxide.

Hafnium alkoxide to water ratio can be in the range from 1:1 to 1:4.

The heating temperature and time of the exemplary synthetic routes described herein for the synthesis of $HfO_2$ nanocrystals can be adjusted such that the reaction temperature can be varied from 250-350° C. while the reaction time can be varied from 20 min-24 hours. Reactions carried out at the lower end of the temperature range may require longer heating times and the reactions carried out at the higher end of this temperature range may require shorter times.

Synthesis of Zinc Oxide (ZnO) Nanocrystals

Organosilane capped zinc oxide nanocrystals were produced as follows. 2.7 grams of zinc acetate dihydrate were dissolved in 140 ml of ethanol and heated to 80° C. with stirring. Once the zinc acetate was completely dissolved and the solution turned clear, the reaction mixture was cooled in an ice-water bath. In a separate flask, a 0.72 gram sample of lithium hydroxide monohydrate was mixed with 60 milliliters of ethanol and sonicated for 30 minutes. This lithium hydroxide/ethanol solution was added drop-wise, at a rate of 3 drops per second, to the zinc acetate dihydrate/ethanol solution in the ice-water bath. Once the entire lithium hydroxide/ethanol solution was added, the reaction mixture was warmed to room temperature and stirred for 1 hour. A 0.25 gram sample of methoxy(triethyleneoxypropyl)trimethoxysilane was mixed with 5 milliliters of ethanol and then injected into the reaction mixture. The entire reaction mixture was stirred for 12 hours at room temperature, forming as-synthesized organosilane-capped zinc oxide nanocrystals. These nanocrystals have a spherical shape with diameters in the 3-6 nm range.

In a further example, larger-sized (equal to or greater than 5 nm and less than 10 nm) organosilane-capped zinc oxide nanocrystals were produced as follows: 2.7 grams of zinc acetate dihydrate was dissolved in 140 milliliters of ethanol and heated to 80° C. with stirring. Once the zinc acetate was completely dissolved and the solution turned clear, the reaction mixture was cooled in an ice-water bath. In a separate flask, a 0.72 gram sample of lithium hydroxide monohydrate was mixed with 60 milliliters of ethanol and sonicated for 30 minutes. This solution was added drop-wise, at a rate of 3 drops per second, to the zinc acetate dihydrate/ethanol solution in the ice-water bath. Once the entire lithium hydroxide/ethanol solution was added, the reaction mixture was placed into a 60° C. hot water bath and stirred for 1 hour. A 0.25 gram sample of methoxytri(ethyleneoxy)propyltrimethoxysilane was mixed with 5 milliliters of ethanol and then injected into the reaction mixture. The entire reaction mixture was stirred for 12 hours at 60° C., forming the as synthesized organosilane capped zinc oxide nanocrystals with diameters equal to or greater than 5 nm and less than 10 nm.

A method of producing organosilane-capped zinc oxide nanocrystals is provided. A 21.28 gram sample of zinc acetate dihydrate is dissolved in 1080 ml of ethanol and heated to ~80° C. with stirring. Once the zinc acetate is completely dissolved and the solution turned clear, the reaction mixture is cooled in an ice-water bath. In a separate flask, a 5.76 gram sample of lithium hydroxide monohydrate is mixed with 480 ml of ethanol and sonicated for 30 minutes. This solution is added drop-wise to the zinc acetate dihydrate/ethanol solution in the ice-water bath. Once the entire lithium hydroxide/ethanol solution is added, the reaction mixture is warmed to room temperature and stirred for 0.5 hours. A 2.0 gram sample of methoxytri(ethyleneoxy)propyltrimethoxysilane is mixed with 15 milliliters of ethanol and then injected into the reaction mixture. The entire reaction mixture is stirred for 16 hours at room temperature, forming as-synthesized organosilane capped zinc oxide nanocrystals. These nanocrystals are spherical with 3-6 nm in diameter.

Alternatively, 4 times more concentrated methoxytri(ethyleneoxy)propyl trimethoxysilane with respect to ethanol was added to the reaction mixture during the synthesis of 3-6 and 5-10 nm ZnO nanocrystals to provided increased capping and dispersibility of the nanocrystals in polar solvents.

Figure 10:
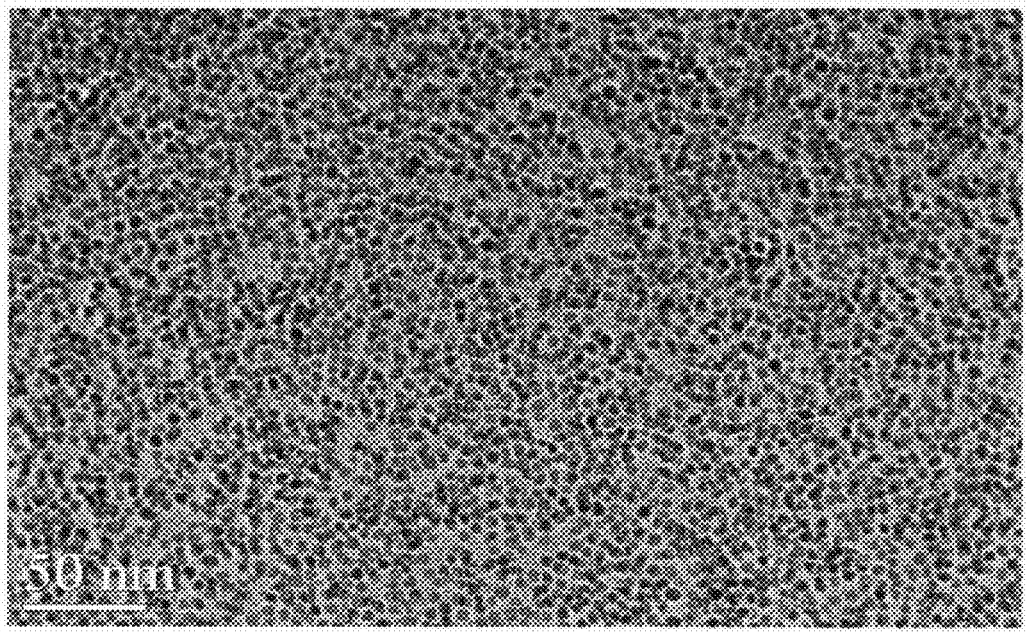
FIG. 10 shows a TEM image of ZnO nanocrystals.

ZnO nanocrystals can be synthesized by another liquid synthetic method. A typical synthesis is as follows: 50 mmol zinc acetate dihydrate was added to 500 ml of absolute ethanol in a flask. The zinc acetate was dissolved completely by heating the flask in a water bath at 80° C. Separately, 200 mmol lithium hydroxide monohydrate was dissolved in 125 ml methanol (or ethanol) at room temperature by vigorous stirring. The LiOH solution was then poured into the refluxing $Zn(Ac)_2$ solution. Following the addition, the heat was removed and the reaction mixture was cooled in air for 20 minutes. A transparent solution resulted. This solution was then re-heated to 80° C. for 30 minutes, until a white precipitate formed. The precipitate is separated from the solution by centrifuging at 4500 rpm at 4° C. for 20 minutes, and washed with THF. A TEM image of the product is shown in FIG. 10.

Alternatively, in the above reactions used to produce ZnO nanocrystals, the molar ratio of the lithium hydroxide to zinc salt can be varied in the range from 1:1.4 to 1:4.

Alternatively, in the above reactions used to produce ZnO nanocrystals, KOH or NaOH can be used as a substitute for lithium hydroxide.

Synthesis of Yttrium Oxide ($Y_2O_3$) Nanocrystals

Yttrium oxide nanocrystals were produced from 1 gram of yttrium oleate and 5.96 grams of dodecylamine which were mixed together and purged with an inert gas for 10 minutes. The reaction mixture was then heated to 70° C. in 20 minutes, maintained at 70° C. for 20 minutes, then further heated to 259° C. in 20 minutes and maintained at 259° C. for 2 hours, with stirring under an inert atmosphere. The reaction mixture was then allowed to cool. At 70° C., 20 ml of ethanol were added to the reaction mixture to precipitate the yttrium oxide nanocrystals.

In another example, yttrium oxide nanodisks (disk-shaped nanocrystals) with a diameter of 20 nanometers were produced from a mixture of 1 gram of yttrium oleate and 5 ml of oleylamine which were mixed and purged with an inert gas such as Argon for 10 minutes. The reaction mixture was then heated to 70° C. in 20 minutes, maintained at 70° C. for 20 minutes, heated to 250° C. in 20 minutes, and finally maintained at 250° C. for 2 hours while stirring under an inert gas atmosphere. The reaction mixture was then allowed to cool. At 70° C., 20 milliliters of ethanol was added to the reaction mixture to precipitate the yttrium oxide nanodisks.

In another example, yttrium oxide nanodisks with a diameter of 10 nanometers were produced from 2 grams of yttrium oleate and 25 ml of oleylamine which were mixed and purged with argon for 10 minutes. The reaction mixture was then heated to 70° C. in 20 minutes, maintained at 70° C. for 20 minutes, heated to 280° C. in 20 minutes, and finally maintained at 280° C. for 2 hours while stirring under argon protection. The reaction mixture was then allowed to cool. At 70° C., 20 milliliters of ethanol was added to the reaction mixture to precipitate the yttrium oxide nanodisks.

In a further example, yttrium oxide nanodisks with a diameter of 10 nanometers were produced from 2 grams of yttrium oleate and 25 ml of oleylamine which were mixed and purged with argon for 10 minutes. The reaction mixture was then heated to 70° C. in 20 minutes, maintained at 70° C. for 20 minutes, heated to 230° C. in 20 minutes, and finally maintained at 230° C. for 2 hours while stirring under argon protection. The reaction mixture was then allowed to cool. At 70° C., 20 milliliters of ethanol was added to the reaction mixture to precipitate out the yttrium oxide nanodisks.

In a further example, yttrium oxide nanocrystals were produced from 2.15 grams of yttrium oleate and 23 grams of dodecylamine which were mixed together and purged with an inert gas for 10 minutes. The reaction mixture was then heated to 70° C. in 20 minutes, maintained at 70° C. for 20 minutes, then heated to 259° C. in 20 minutes and maintained at 259° C. for 2 hours, with stirring under an inert atmosphere. The reaction mixture was then allowed to cool. At 70° C., 20 milliliters of ethanol was added to the reaction mixture to precipitate the yttrium oxide nanocrystals. The product has a flake-like shape, where the flakes have a thickness of 2 nm.

Example 2

Removing Ligands from Surface of Nanocrystals

Hydrochloric acid treatment of the as-synthesized $HfO_2$ and $ZrO_2$ nanocrystal surface may be necessary to remove the organic moieties or capping agents which are on the surface of the nanocrystals before any further modification is possible. An exemplary method includes suspending as-synthesized or purified nanocrystals in water by stirring and adjusting the suspension to a pH of 1 using a 1 M hydrochloric acid solution. The solution changes from a milky white suspension to a transparent solution upon the addition of hydrochloric acid. The solution may be stirred overnight at room temperature to allow the reaction to progress further. When the solution is added to tetrahydrofuran, a white solid precipitates. After centrifugation, the precipitate can be collected. The process of re-suspending the particles in tetrahydrofuran and then centrifuging the mixture and collecting the precipitate may be repeated until the pH of the supernatant is in the 5-7 range.

Example 3

Cap Exchange of Nanocrystals

Cap Exchange of $ZrO_2$, $HfO_2$ and $TiO_2$—$ZrO_2$ Nanocrystals

After the synthesis of the $ZrO_2$, $HfO_2$ and $TiO_2$—$ZrO_2$ nanocrystals, the as-synthesized nanocrystals are transferred into a round bottom flask to perform the cap exchange. The as-produced nanocrystals may be capped by the solvent or reaction by-products that are present during synthesis. It may be desirable to exchange the capping molecules of the nanocrystals for a variety of reasons, including, but not limited to: increased dispersibility in solvent or some other matrix, having different optical properties, or having different chemistry at the surface of the nanocrystals. The cap exchange process may involve dispersing or suspending the as-synthesized nanocrystals in a solvent or reaction mixture along with a certain amount of capping agents. This reaction may be carried out at an elevated temperature and for a certain amount of time in order to promote cap exchange. A non-limiting list of choices for capping agents to perform the cap exchange on the as-synthesized $ZrO_2$, $HfO_2$ and $TiO_2$—$ZrO_2$ nanocrystals includes: methoxytri(ethelyneoxy)propyltrimethoxy silane, 2-[2-(2-methoxyethoxy)ethoxy]acetic acid, 3-(methacryloyloxy)propyl trimethoxysilane and other silanes, carboxylic acids and alcohols. The cap exchange may be carried out in benzyl alcohol or other solvent or mixtures of solvents.

Cap exchange of the as-synthesized $ZrO_2$, $HfO_2$ and $TiO_2$—$ZrO_2$ nanocrystals may be carried out using methoxytri(ethelyneoxy)propyltrimethoxy silane as the capping agent. The methoxytri(ethelyneoxy)propyltrimethoxy silane may be injected into a reaction vessel (typically a round bottom flask) containing the as-synthesized nanocrystals reaction mixture. The weight ratio of methoxytri(ethelyneoxy)propyltrimethoxy silane to the as synthesized nanocrystals may range from 1:5 to 3:2. Then the mixture is heated to 80-150° C. for an interval that may be as short as 10 minutes or as along as 3 hours. A typical procedure for a methoxy(triethelyneoxy)propyltrimethoxy silane cap exchange on as-synthesized nanocrystals involves the following: 1 g of methoxy(triethelyneoxy)propyltrimethoxysilane capping agent was added to a round bottom flask which holds the reaction mixture containing 5 g of as-synthesized $ZrO_2$, $HfO_2$ or $TiO_2$—$ZrO_2$ nanocrystals. During the addition of the capping agent the mixture was stirred continuously. The suspension was heated up to 80-150° C. and kept at that temperature while continuing to stir for 10 min-1 hour. Afterwards, the reaction was allowed to cool to room temperature.

Alternatively, the cap exchange of the $ZrO_2$, $HfO_2$ and $TiO_2$—$ZrO_2$ nanocrystals with methoxy(triethelyneoxy)propyltrimethoxy silane as the capping agent may be carried out on suspensions of nanocrystals other than the as-synthesized reaction mixture. Similar reactions may be carried out on suspensions of nanocrystals including, but not limited to, suspensions containing: nanocrystals which have previously undergone cap-exchange, as-synthesized nanocrystals which have previously undergone purification, nanocrystals which have had the capping agents removed by acid treatment, and nanocrystals which have been transferred to different solvents. Alternative solvents for cap exchange may be chosen from a list including, but not limited to: benzyl alcohol, propylene glycol monomethyl ether (PGME), propylene glycol methyl ether acetate (PGMEA), ethyl lactate (EL), and 2-propoxy-propanol (PnP), acetone, tetrahydrofuran, phenol, oleyl alcohol, toluene, butanol, propanol, isopropanol, ethanol, water and mixtures thereof.

Cap exchange of the as-synthesized $ZrO_2$, $HfO_2$ and $TiO_2$—$ZrO_2$ nanocrystals may be carried out using 2-[2-(2-methoxyethoxy)ethoxy]acetic acid as the capping agent. The 2-[2-(2-methoxyethoxy)ethoxy]acetic acid may be injected into a reaction vessel (typically a round bottom flask) containing the as-synthesized nanocrystals reaction mixture. The amount of 2-[2-(2-methoxyethoxy)ethoxy]acetic acid may be as little as 0.4 g or may be as much as 1.5 g per gram of as-synthesized $ZrO_2$, $HfO_2$ or $TiO_2$—$ZrO_2$ nanocrystals. Then the mixture may either be kept at a temperature as low as 20° C. or heated as high as 50° C. for an interval that may be as short as 30 minutes or as along as 3 hours. A typical procedure for a 2-[2-(2-methoxyethoxy)ethoxy]acetic acid cap exchange reaction performed on as-synthesized nanocrystals involves the following: 2 g of 2-[2-(2-methoxyethoxy)ethoxy]acetic acid is added to a round bottom flask which holds the reaction mixture containing 5 g of as-synthesized nanocrystals. During the addition the mixture is stirred continuously. The suspension is kept at room temperature while continuing to stir for 1 hour.

Alternatively, the cap exchange of the $ZrO_2$, $HfO_2$ and $TiO_2$—$ZrO_2$ nanocrystals with 2-[2-(2-methoxyethoxy)ethoxy]acetic acid as the capping agent may be carried out on suspensions of nanocrystals other than the as-synthesized reaction mixture. Similar reactions may be carried out on suspensions of $ZrO_2$, $HfO_2$ or $TiO_2$—$ZrO_2$ nanocrystals including, but not limited to, suspensions containing: nanocrystals which have previously undergone cap-exchange, as-synthesized nanocrystals which have previously undergone purification, nanocrystals which have had the capping agents removed by acid treatment, and nanocrystals which have been transferred to different solvents. Alternative solvents for cap-exchange reactions may be chosen from a list including, but not limited to: benzyl alcohol, propylene glycol monomethyl ether (PGME), propylene glycol methyl ether acetate (PGMEA), ethyl lactate (EL), and 2-propoxy-propanol (PnP), acetone, tetrahydrofuran, phenol, oleyl alcohol, toluene, butanol, propanol, isopropanol, ethanol, water, cyclic ketones and mixtures thereof.

Cap exchange of the as-synthesized $ZrO_2$, $HfO_2$ and $TiO_2$—$ZrO_2$ nanocrystals may be carried out using 3-(methacryloyloxy)propyl trimethoxysilane as the capping agent. The 3-(methacryloyloxy)propyl trimethoxysilane may be injected into a reaction vessel (typically a round bottom flask) containing the as-synthesized nanocrystals reaction mixture. The amount of 3-(methacryloyloxy)propyl trimethoxysilane may be as little as 0.8 g or may be as much as 1.5 g per gram of as-synthesized nanocrystals. Then the mixture is heated to 120° C. for an interval that may be as short as 30 minutes or as along as 1 hour. A typical procedure for a 3-(methacryloyloxy)propyl trimethoxysilane cap exchange performed on as-synthesized nanocrystals involves the following: 4 g of 3-(methacryloyloxy)propyl trimethoxysilane is added to a round bottom flask which holds the reaction mixture containing 5 g of as-synthesized $ZrO_2$, $HfO_2$ or $TiO_2$—$ZrO_2$ nanocrystals. During the addition of the capping agent the mixture is stirred continuously. The suspension is heated up to 120° C. and kept at that temperature while continuing to stir for 1 hour. Afterwards, the reaction is allowed to cool to room temperature.

Alternatively, the cap exchange of the $ZrO_2$, $HfO_2$ and $TiO_2$—$ZrO_2$ nanocrystals with 3-(methacryloyloxy)propyl trimethoxysilane as the capping agent may be carried out on suspensions of nanocrystals other than the as-synthesized reaction mixture. Similar reactions may be carried out on suspensions of nanocrystals including, but not limited to, suspensions containing: nanocrystals which have previously undergone cap-exchange, as-synthesized nanocrystals which have previously undergone purification, nanocrystals which have had the capping agents removed by acid treatment, and nanocrystals which have been transferred to different solvents. Alternative solvents for dispersion of the nanocrystals during the cap exchange reaction may be chosen from a list including, but not limited to: benzyl alcohol, propylene glycol monomethyl ether (PGME), propylene glycol methyl ether acetate (PGMEA), ethyl lactate (EL), and 2-propoxy-propanol (PnP), acetone, tetrahydrofuran, phenol, oleyl alcohol, toluene, butanol, propanol, isopropanol, ethanol, water, cyclic ketones and mixtures thereof.

Cap exchange of the as-synthesized $ZrO_2$, $HfO_2$ and $TiO_2$—$ZrO_2$ nanocrystals may be carried out using 3-(methacryloyloxy)propyl trimethoxysilane and methoxy(triethelyneoxy)propyltrimethoxy silane as capping agents. An exemplary cap exchange reaction of $ZrO_2$ nanocrystals is as follows: 500 mg as synthesized $ZrO_2$ was mixed with 25 mg 3-(methacryloyloxy)propyl trimethoxysilane in 5 ml PGMEA at 100° C. for 1 hour. 150 mg bf methoxy(triethelyneoxy)propyltrimethoxy silane is then added to the suspension and the mixture was stirred at 100° C. for another hour. The product mixture was washed with heptanes and white precipitate is collected.

The as-produced nanocrystals of $ZrO_2$, $HfO_2$ and $TiO_2$—$ZrO_2$ may also be capped in order to facilitate dispersion in hydrophobic solvents and matrices. The cap exchange process may involve dispersing or suspending the as-synthesized nanocrystals, along with a certain amount of capping agent or capping agents, in a relatively hydrophobic solvent, chosen from a list of solvents including but not limited to: naptha, toluene, heptane, pentane, decane, chloroform. This cap exchange reaction may be carried out at room temperature or an elevated temperature and for an amount of time ranging from a few minutes to days in order to promote cap exchange. A list of choices for capping agents that may make the surface of the as-synthesized $ZrO_2$, $HfO_2$ and $TiO_2$—$ZrO_2$ nanocrystals more compatible with hydrophobic solvents and media includes, but is not limited to: stearic acid, oleic acid, and octadecyltrimethoxysilane. In a typical reaction: 2 g oleic acid is added to a suspension containing 2 g of as-synthesized nanocrystals in 20 ml of toluene. During and after the addition of the capping agent the mixture is continuously stirred. The reaction mixture is allowed to react for between several minutes and several hours before purification is then carried out.

Cap exchange of the as-synthesized $ZrO_2$, $HfO_2$ and $TiO_2$—$ZrO_2$ nanocrystals may be carried out using methoxy-poly(ethelyneoxy)propyltrimethoxy silane as capping agent. Alternatively, the cap exchange of the $ZrO_2$, $HfO_2$ and $TiO_2$—$ZrO_2$ nanocrystals with methoxypoly(ethelyneoxy)propyltrimethoxy silane as the capping agent may be carried out on suspensions of nanocrystals other than the as-synthesized reaction mixture. Similar reactions may be carried out on suspensions of nanocrystals including, but not limited to, suspensions containing: nanocrystals which have previously undergone cap-exchange, as-synthesized nanocrystals which have previously undergone purification, nanocrystals which have had the capping agents removed by acid treatment, and nanocrystals which have been transferred to different solvents. Alternative solvents for dispersion of the nanocrystals during the cap exchange reaction may be chosen from a list including, but not limited to: benzyl alcohol, propylene glycol monomethyl ether (PGME), propylene glycol methyl ether acetate (PGMEA), ethyl lactate (EL), and 2-propoxy-propanol (PnP), acetone, tetrahydrofuran, phenol, oleyl alcohol, toluene, butanol, propanol, isopropanol, ethanol, water, cyclic ketones and mixtures thereof.

Cap-Exchange of Yttrium Oxide Nanocrystals

Organosilane capped yttrium oxide nanocrystals can be produced via a cap exchange process involving as synthesized yttrium oxide nanocrystals and methoxy(triethyleneoxy)propyltrimethoxysilane. As-produced yttrium oxide nanocrystals and methoxytri(ethyleneoxy)propyltrimethoxysilane were mixed together in tetrahydrofuran. The mixture was then heated to 200° C. for 2-4 hours inside an autoclave. After the reaction time expired the mixture was allowed to cool to room temperature.

Alternatively the cap exchange process may be carried of other organosilanes, organocarboxylic acids and organoalcohols. Similar reactions may be carried out on suspensions of nanocrystals including, but not limited to, suspensions containing: nanocrystals which have previously undergone cap-exchange, as-synthesized nanocrystals which have previously undergone purification, nanocrystals which have had the capping agents removed by acid treatment, and nanocrystals which have been transferred to different solvents. Alternative solvents for dispersion of the nanocrystals during the cap exchange reaction may be chosen from a list including, but not limited to: benzyl alcohol, propylene glycol monomethyl ether (PGME), propylene glycol methyl ether acetate (PGMEA), ethyl lactate (EL), and 2-propoxy-propanol (PnP), acetone, phenol, oleyl alcohol, toluene, butanol, propanol, isopropanol, ethanol, water, cyclic ketones and mixtures thereof.

Cap-Exchange of ZnO Nanocrystals

When the ZnO nanocrystals are synthesized without the addition of a capping agent during the synthesis, they can be capped after the synthesis is complete with 3-(methacryloyloxy)propyl trimethoxysilane, methoxytri(ethelyneoxy)propyltrimethoxy silane, 2,2,2-methyoxyethyoxyethyoxy-acetic acid or a combination of these materials. The capping with 2,2,2-methyoxyethyoxyethyoxy-acetic acid can be carried out at room temperature or with the aid of sonication or heating of the suspension to 80° C. or with a combination of both heating and sonication. A typical method is as follows: After the synthesis 4 g of as-synthesized precipitate is re-dispersed in PGMEA in a round bottom flask. To this suspension 2 g of 2,2,2-methyoxyethyoxyethyoxy-acetic acid is added while stirring. The suspension is then exposed to brief (<1 minute) sonication to aid in the capping reaction. The capped nanocrystals are then precipitated out with THF and heptane, with the 1:1:3 volume ratio of nanocrystal:THF:heptane. The precipitates are collected by centrifugation at 6500 rpm.

Example 4

Purifying Nanocrystals

As-synthesized $ZrO_2$, $HfO_2$ and $TiO_2$—$ZrO_2$ Nanocrystals

The as synthesized white milky nanocrystal suspension collected after the autoclave synthesis of the $ZrO_2$, $HfO_2$ and $TiO_2$—$ZrO_2$ nanocrystals can be purified. An exemplary method includes mixing the suspensions of nanocrystals with ethanol and centrifuging (8000 rpm for 30 minutes) to separate the nanocrystals. After decanting and discarding the supernatant, a white precipitate is collected. The wet nanocrystals are suspended in additional ethanol by sonication, stirring or shaking and suspension is centrifuged again. These resuspension steps, which consist of ethanol addition, centrifugation and collection of the resultant powder are repeated as many as 4 more times to obtain purified nanocrystals.

$ZrO_2$ Nanocrystals with Hydrophobic Surface

To purify the nanocrystals they are dispersed in hexane, and then precipitated out using ethanol as the antisolvent. The resultant mixture is then centrifuged and the nanocrystals are collected. This purification process is repeated three times to get nanocrystals that are easily dispersible into hydrophobic solvents such as naphtha and heptane.

$ZrO_2$, $HfO_2$ and $TiO_2$—$ZrO_2$ Nanocrystals

After synthesis, capping and or cap exchange, $ZrO_2$, $HfO_2$ and $TiO_2$—$ZrO_2$ nanocrystals may be purified or further purified. One exemplary purification of the nanocrystals after being synthesized in benzyl alcohol or mixture of benzyl alcohol with other solvents may include: addition of THF to the reactions mixture in a 2:1 volume ratio of THF to the reaction mixture followed by addition of heptane in a 7-9 to 1 volume ratio of heptane to the reaction mixture. The reaction of nanocrystal suspension to THF to heptane may be adjusted based on the nanocrystal concentration in the suspension. This causes the precipitation of the nanocrystals which are then centrifuged. After centrifugation and the decanting of the supernatant, additional amounts of THF or PGMEA is added to disperse the nanocrystals followed by addition of heptane. Heptane to THF or PGMEA ratio may be 2:1 or 3:1. Cycles of sonication, centrifugation and decantation is repeated 2-5 times to purify the nanocrystals.

ZnO Nanocrystals

As-synthesized, capped and/or cap-exchanged zinc oxide nanocrystals may be purified or further purified to obtain an optically clear suspension in a polar solvent. This process removes at least part of the by-product of the synthesis or cap exchange reactions. An exemplary method of purifying the ZnO nanocrystals is as follows: A suspension of 200 ml zinc oxide nanocrystals in ethanol (~1 g ZnO) is mixed with 400-500 milliliters of heptane to form a white precipitate which is collected by centrifugation, followed by decanting and discarding the supernatant. A sample of 20-60 milliliters of ethanol is then used to redisperse the white precipitate into solution with 5 minutes of ultrasonication, and a sample of 40-50 milliliters of heptane was used again to precipitate the product. After collecting the white precipitate by centrifugation, the decanting and discarding of the supernatant was repeated for a second time. The ethanol redispersion/heptane precipitation procedure was repeated twice more to obtain a purified nanocrystals.

In a further example, capped zinc oxide nanocrystals were purified to obtain re-dispersable dry powders. A suspension of 200 ml organosilane capped zinc oxide nanocrystals in ethanol (~1 g ZnO) was mixed with 400-500 ml of heptane to form a white precipitate. This white precipitate was collected by centrifugation, followed by the decanting and discarding of the supernatant. A sample of 20 ml of ethanol was then used to redisperse the white solid, with the aid of 5 minutes of ultasonication. 40-50 ml of heptane was used to once again precipitate the product. After collecting the white precipitate by centrifugation, and decanting and discarding the supernatant for a second time, the ethanol redispersion/heptane precipitation procedure was repeated, preferably, twice more. A sample of 5 ml of pentane was then added to the washed organosilane capped ZnO nanocrystals and ultrasonicated for 5 minutes. The resulting mixture was then centrifuged again and the precipitate was again collected. After discarding the supernatant, the solid was dried in air or under vacuum, resulting in a dry white precipitate which is a ZnO nanocrystalline powder.

Another method of purifying the as-synthesized organosilane capped zinc oxide nanocrystals to obtain an optically clear suspension in a polar solvent is provided. When 1.6 L of the as prepared organosilane capped zinc oxide nanocrystal/ethanol suspension, containing >8 g ZnO, is mixed with 3.2-4.0 L of heptane, a white precipitate forms. This white precipitate is collected by centrifugation, followed by the decanting and discarding of the supernatant. A sample of 60 ml of ethanol is then used to redisperse the white precipitate with the aid of 5 minutes of ultrasonication. 120-150 ml of heptane are used again to precipitate the product. After collecting the white precipitate by centrifugation, followed by decanting and discarding the supernatant for a second time, ~8 g of organosilane capped ZnO nanocrystals are obtained. To achieve even higher purity the ethanol redispersion/heptane precipitation procedure is repeated twice more resulting in a white precipitate.

$Y_2O_3$ Nanocrystals

The purification of as-synthesized $Y_2O_3$ nanocrystals may involve the following: As-synthesized reaction mixture was precipitated with addition of 4:1 volume percent ethanol to the reaction mixture. The suspension was centrifuged at 9000 rpm for 20 minutes and afterwards the supernatant was decanted and discarded while the precipitate was collected. This precipitate was then suspended in 2 ml of chloroform via sonication (>1 minute) and re-precipitated by the addition of 2 ml of ethanol. The suspension was centrifuged at 9000 rpm for 30 minutes, after which the supernatant was again decanted and discarded while the precipitate was collected. The precipitate was dispersed in 3 ml of hexane via sonication (>2 minutes) and re-precipitated with 2 ml of ethanol, where the supernatant was decanted and discarded while the precipitate was collected. The redispersion-precipitation procedure using hexane and ethanol was repeated once more. After this purification procedure, the yttrium oxide nanocrystals can be dispersed into a number of solvents, such as chloroform, hexane, toluene and tetrahydrofuran.

The purification of the $Y_2O_3$ nanocrystals after the cap exchange reaction may involve the following: The nanocrystals were precipitated with pentane and centrifuged at 9000 rpm for 20 minutes. The precipitate was re-dispersed in tetrahydrofuran, precipitated with hexane and centrifuged at 9000 rpm for 20 minutes to remove the excess capping agent and by-products. The precipitate can be dispersed into a variety of solvents, such as tetrahydrofuran, chloroform and toluene and mixtures of solvents such as hexane and ethanol.

Example 5

Nanocomposite Formation

Formation of Nanocomposites Suspensions and Nanocomposite Layers from Capped ZnO Nanocrystals and Polymers Capped and purified ZnO nanocrystals, in the form of a white precipitate or nanocrystalline powders, may be dispersed in a number of polar solvents, including, but not limited to, tetrahydrofuran, ethanol, methanol, acetonitrile, PGMEA, PGME, PGPE, ethyl lactate, cyclic ketones and acetone, to form optically transparent suspensions. These optically transparent suspensions can be mixed with various polymer solutions to form uniformly dispersed ZnO/polymer nanocomposites using solvent mixing. The dispersion solvent for the nanocrystals may be selected based on the chemical compatibility of the capping agent and the polymer. A solvent system that is suitable for dispersing both the nanocrystals and the polymer is preferred. To form the composite solution in the desired nanocrystal to polymer ratio, the nanocrystals that are dispersed in the selected solvent are mixed with a separately prepared solution of the polymer preferably in the same solvent or a different solvent, or a combination of solvents compatible with the selected solvent. These polymers include, but are not limited to, PMMA, JSR topcoat, JSR Micro (CA) brand acrylate based photoresists, Honeywell spin-on glass polymers (silicon based polymer, from Honeywell Electronic Materials, CA), PEO (polyethylene oxide), epoxy resins, silicones such as Polydimethylsiloxane (PDMS) and polymethylphenylsiloxane, and epoxy resins.

An exemplary method of forming a nanocomposite suspension provides mixing a sample of 38 milligrams of purified capped ZnO nanocrystal powder with 0.5 grams of Honeywell Electronic Material (HEM) Spin-on-Glass (SOG) polymer/ethanol solution (HW SOG, solid content is 1-5% by weight). This mixture was ultrasonicated for 30 minutes, resulting in an optically transparent suspension.

Similarly, highly transparent films were obtained with epoxy or acrylic polymers or spin-on-glasses and $ZrO_2$ nanocrystals with 5 nm average size. The nanocrystal weight loading can be varied from 0.01 to 90 percent, resulting in an optically transparent suspensions and films.

A suspension of capped ZnO nanocrystals with average particle size of 3 to 4 nm mixed with SOG in ethanol was used to prepare a nanocomposite film by spin-coating the suspension on a 2 inch quartz disc at a spin rate of 500 rpm to determine the film uniformity of the resulting nanocomposite. UV-Vis spectroscopy was used to measure the optical density (OD) of the film at different spots along 3 radial directions. The center of the disc was marked as 0 mm and measurements were taken at 0, 3, 5, 8, 12, 16, and 20 mm from the center. The exciton peak showed a maximum at 330 nm and the deviation in the OD at 330 nm was less than 2.0% for all the measurement.

Figure 11:
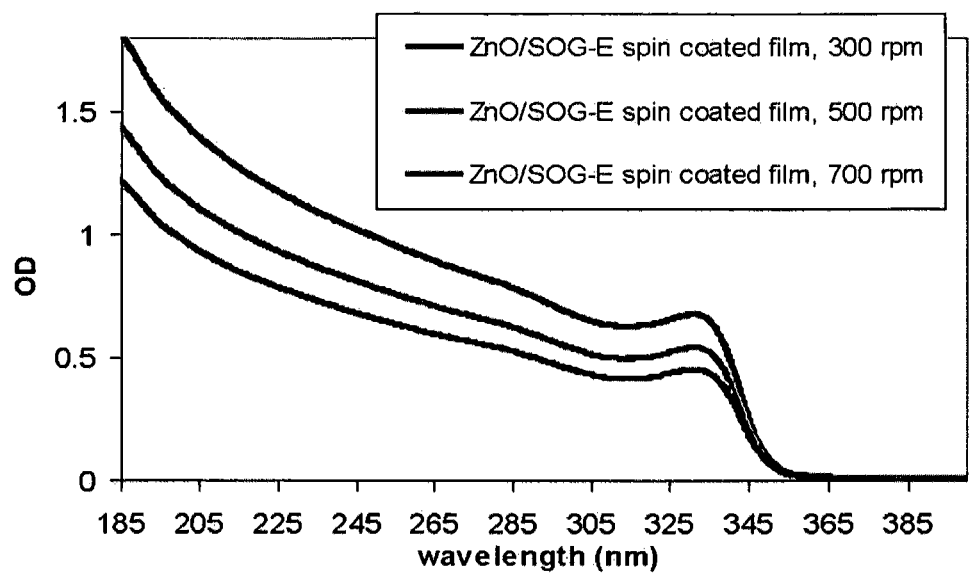
FIG. 11 shows the UV-Vis spectra of a ZnO/SOG nanocomposite spin coated films.

The suspension of capped ZnO nanocrystals mixed with SOG in ethanol was also used to spin-coat a film on three 1" quartz discs at 300, 500 and 700 rpm respectively. These films were baked at 80° C. for 1 minute in air in order to remove residual ethanol. The resultant films were visually transparent with no apparent haze or opaqueness. The nominal loading of ZnO nanocrystals in the SOG polymer nanocomposite was measured to be 72.0% by weight, as calculated from the nanocomposite composition. FIG. 11 shows the UV-Vis spectra of the resulting films. These nanocomposite films all have a band gap maximum at around 330 nm wavelength corresponding to the exciton peak of ZnO. As the spin rate at which the film was cast increased from 300 rpm to 700 rpm, the optical density (OD) of the films decreased due to the decreasing film thickness. The nanocomposite films are highly transparent at visible wavelengths, as indicated by the lack of scattering above 350 nm and sharp exciton peaks in the UV-Vis spectra.

Figure 12:
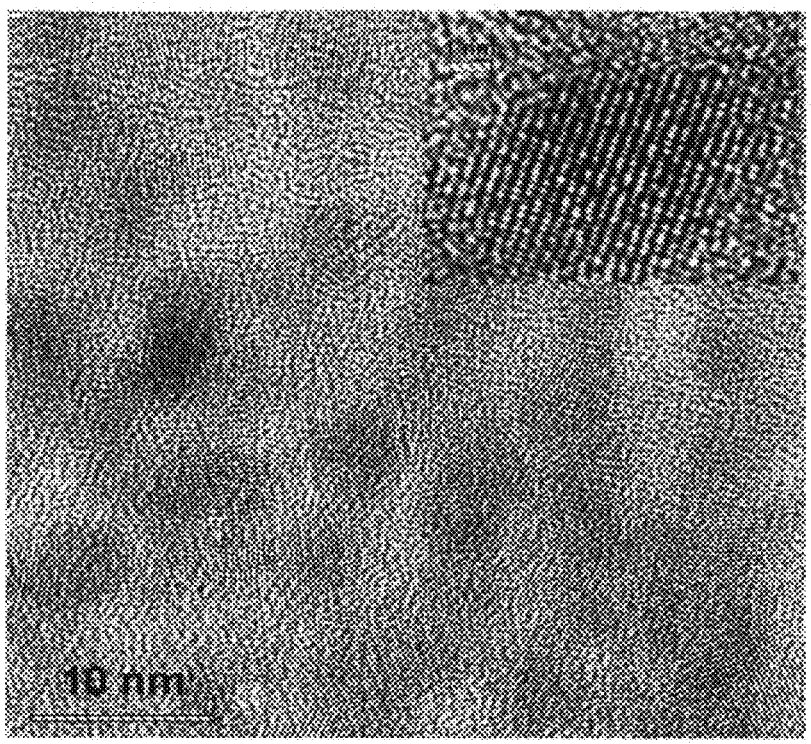
FIG. 12 shows the TEM images of a ZnO/PMMA nanocomposite.

A method of forming a nanocomposite includes solvent mixing purified capped zinc oxide nanocrystals of the present disclosure with PMMA in tetrahydrofuran. The purified capped ZnO nanocrystals were dispersed in tetrahydrofuran and then mixed with a PMMA/THF solution. FIG. 12 shows the TEM of the nanocomposite that was spin coated on a Cu TEM grid. The scale bar on the TEM image is 10 nm and the 4-5 nm capped ZnO nanocrystals are uniformly dispersed into the PMMA matrix without forming any aggregates. The inset shows a close-up of a single nanocrystal in the nanocomposite.

The organosilane capped ZnO nanocrystals dispersed in PMMA/THF solution was used to prepare a nanocomposite film by spin-coating on a 2 inch silicon wafer at a spin rate of 500 rpm. The film thickness measurements were done by Dektak profilometer. For this measurement periodic scratches were made on the film to determine the film thickness. A 1 mm distance was measured showing a uniform film thickness of ~300 nm with a thickness variation of <3% over this range.

Another example of a method of forming a nanocomposite of the present disclosure includes dispersing purified capped zinc oxide nanocrystals of the present disclosure with an epoxy polymer in tetrahydrofuran. 500 mg of as-purified organosilane capped ZnO nanocrystals were dispersed into 2 ml tetrahydrofuran and mixed with 1.5 g epoxy, EPON™ Resin 862 (Diglycidyl Ether of Bisphenol F) which is a low viscosity, liquid epoxy resin and 0.3 g Epikure™ W (Epikure W is an aromatic diamine curing agent for epoxy resin) curing agent. The mixture was transferred into a mold and cured for 12 hours, and then post-cured at 150° C. for 3 hours.

Another example of a method of forming a nanocomposite of the present disclosure includes mixing resin EPON 862 and curing agent W (or curing agent 3295) by hand using a weight ratio of 5:1. To this mixture ZnO or $ZrO_2$ capped with methoxytri(ethyleneoxy)propyltrimethoxysilane is then added. The weight ratio of the nanocrystals to the epoxy mixture can be range from 1:1000 to 10:1. A small amount of THF (no more than 200 wt % of the composite mixture) was added to reduce the viscosity of the nanocrystal/epoxy resin mixture. The mixture is then sonicated either inside a sonication bath or using a Hielscher UP200S sonication probe for less than five minutes. After sonication, the composite mixture (2 gram to 4 grams) was then poured into an aluminum pan (4 cm diameter), which acted as a mold. The loaded pan was and placed inside a vacuum oven. Vacuum was applied in order to remove the THF and air bubbles. The oven was then heated to 80° C. for overnight (>10 hr) under vacuum. The resulting composite was post cured at 150° C. for another 3 hours before it was removed from the vacuum oven.

Another example of a method of forming a nanocomposite of the present disclosure may be as follows: epoxy resin EPON 862 and curing agent 3274 were pre-mixed by hand using weight ratio of 10:4. 3-(methacryloyloxy)propyl trimethoxysilane capped $ZrO_2$ nanocrystals are then added into the epoxy resin at loading levels between 0.01-99.99 wt %. A small amount of acetone (no more than 200 wt % of the composite mixture) was added to reduce the viscosity of the nanocrystal/epoxy resin mixture. The mixture is then sonicated either inside a sonication bath or using a Hielscher UP200S sonication probe for less than five minutes. The mixed composite mixture (2 gram to 4 grams) was then poured into an aluminum pan (4 cm diameter), which acted as a mold. The loaded pan was then placed inside a vacuum oven. Vacuum was applied to remove the acetone and air bubbles. The resulting composite was cured at room temperature for 24 hours before it was removed from the vacuum oven.

For spin coating 3-(methacryloyloxy)propyl trimethoxysilane capped nanoparticle/epoxy composite films, a typical protocol is described as follows: epoxy resin EPON 862 and curing agent 3274 were pre-mixed by hand using weight ratio of 10:4. The desired amount of capped nanocryastals is then added into the epoxy resin at loading levels between 1-99.99 wt %. Acetone was added to prepare a spin solution with an appropriate solid content (ranging from 10 wt % to 50 wt %). The mixture is then sonicated inside a sonication bath for 5 minutes. The solution can then be used directly for spin-coating. By varying the spin-rate different film thicknesses ranging from several hundred nanometers to several micrometers may be achieved.

Another example of forming a nanocomposite of the present disclosure includes solvent mixing of purified capped zinc oxide nanocrystals of the present disclosure with a photoresist from JSR Micro Inc. The as-purified capped ZnO nanocrystals were dispersed into PGMEA to form a clear suspension and JSR photoresist solution is mixed with this suspension. The resultant suspension forms a nanocomposite film after spin coating on a surface.

In a further example, a nanocomposite of the present disclosure is formed by solvent mixing purified capped zinc oxide nanocrystals of the present disclosure with a topcoat polymer from JSR Micro Inc. The as-purified organosilane capped ZnO nanocrystals were dispersed in 4-methyl-2-pentanol which was also the solvent in the JSR topcoat polymer solution. The nanocrystal suspension was mixed with the topcoat solution to form a dispersion which can be used to form a nanocomposite film by spin-coating on a surface.

The method of the disclosure includes dispersing the purified capped zinc oxide nanocrystals in water. The as-purified capped ZnO nanocrystals were dispersed into water by mixing the wet precipitate of ZnO after purification and water to form a clear suspension by sonication. This suspension was mixed with JSR aqueous topcoat solution (NFC 545-34).

Figure 13:
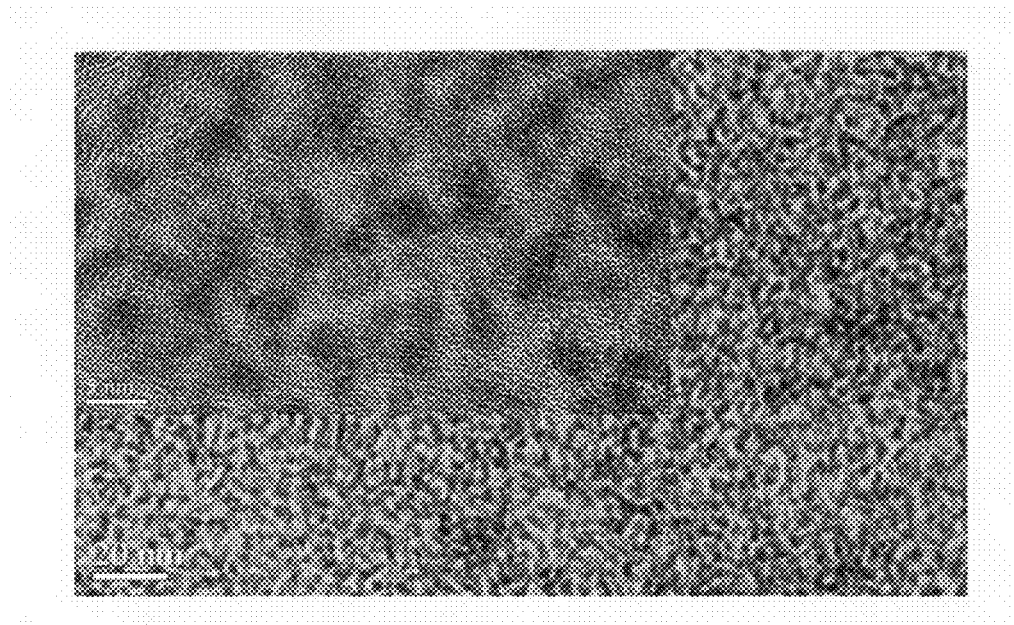
FIG. 13 shows the TEM images of a $HfO_2$/SOG nanocomposite.

In a further example, a nanocomposite of the present disclosure is formed by dispersing methoxytri(ethyleneoxy)propyltrimethoxysilane capped $HfO_2$ nanocrystals in ethanol to form a suspension and mixing this suspension with a SOG/ethanol solution. FIG. 13 shows the TEM images of the nanocomposite prepared by spin coating the suspension on a Cu TEM grid. The figure inset shows a close up of the nanocrystals. These images show that the 45 nm rice-shaped $HfO_2$ nanocrystals were uniformly dispersed in the SOG matrix with no visible aggregate formation.

Figure 14:
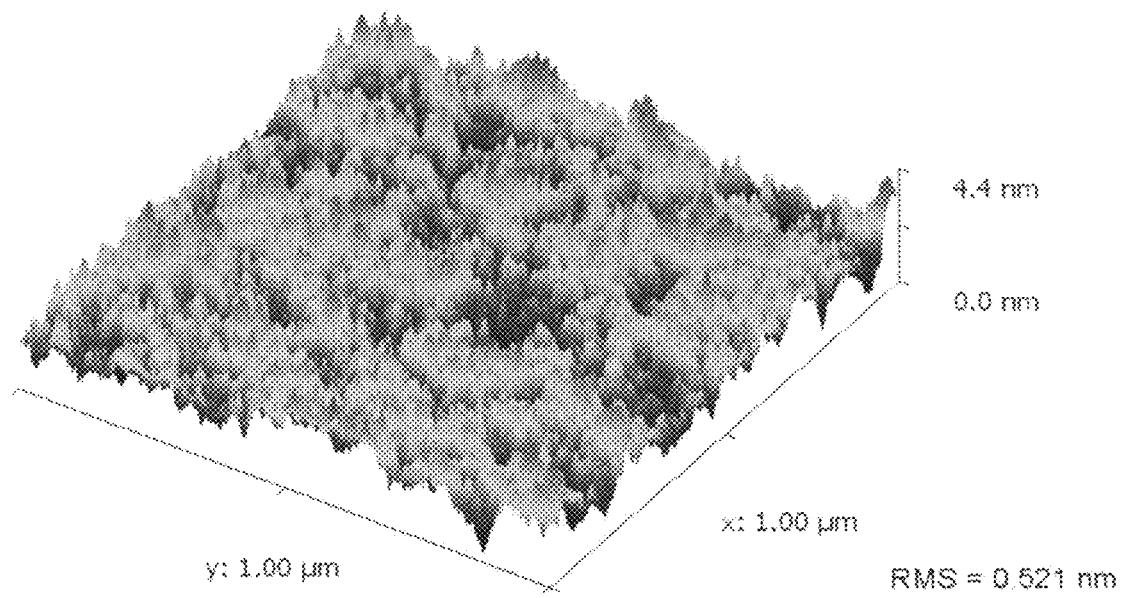
FIG. 14 shows surface roughness of a $ZrO_2$ film as measured by AFM.

A further example of forming a nanocomposite of the disclosure involves dispersing methoxytri(ethyleneoxy)propyltrimethoxysilane capped $ZrO_2$ nanocrystals of the disclosure and an acrylate based polymer in a mixture of PGMEA and PGME to form a nanocomposite suspension. Films of this suspension are made by spin coating on quartz discs and silicon wafers. The loading of the nanocrystals in the polymer matrix is up to 80 wt %. The films are made after the nanocomposite suspension is filtered through a 200 nm filter. FIG. 14 shows the AFM image indicating the surface roughness of a nanocomposite film prepared by spin coating the suspension on a quartz disc. The Root Mean Square (RMS) roughness value for this film was 0.521 nm.

In-Situ Polymerization

Nanocomposite of $ZrO_2$ nanocrystals and polymethyl methacrylate can be prepared by in-situ polymerization of methyl methacrylate (MMA) and nanocrystals which are at least partially capped with 3-(methacryloyloxy)propyl trimethoxysilane. A typical synthesis protocol of the nanocomposite is described as follows: 500 mg MMA and 2 mg AIBN are dissolved in 9 g toluene and the solution is heated to 100° C. 0.5 g of $ZrO_2$ nanocrystals capped with a mixture of both 3-(methacryloyloxy)propyl trimethoxysilane and methoxytri(ethyleneoxy)propyltrimethoxysilane is dispersed in 1 g of THF. This dispersion is added into the MMA/toluene solution drop-wise. The mixture was maintained at 100° C. for 16 h. The reaction mixture is slightly cloudy. The resulting precipitate is collected by anti-solvent precipitation using methanol. The precipitate is then redispersed into THF to form a 12 wt % dispersion. Approximately 38 wt % of the solid content of this dispersion is from the capping agents and the PMMA according to thermogravimetric analysis (TGA) of the product.

Another example of nanocomposite formed by in situ polymerization of $ZrO_2$ nanocrystals and polymethyl methacrylate is as follows: 9 g of toluene is heated to 100° C. 0.5 g 3-(methacryloyloxy)propyl trimethoxysilane and methoxytri(ethyleneoxy)propyl trimethoxysilane capped $ZrO_2$ nanocrystals, 0.5 g MMA and 2 mg AIBN are added to 1 g THF. This mixture is added into the hot toluene drop-wise. The mixture was maintained at 100° C. for 16 h, after which the reaction mixture is slightly cloudy. The resulting nanocomposite is collected by anti-solvent precipitation using methanol. The precipitate is then redispersed into THF to form a 5 wt % dispersion. Approximately 31 wt % of the solid content of this dispersion is due to the capping agents and the PMMA according to TGA of the product.

We claim:
1. A solvothermal method of making nanocrystals comprising
    dissolving or mixing at least one precursor of said nanocrystals in at least one solvent to produce a solution,
    heating said solution to a temperature in the range of 250° C. to 350° C. to form said nanocrystals, wherein
said at least one solvent additionally includes water, and
said nanocrystals are comprised of at least one of hafnium oxide, zirconium oxide, hafnium-zirconium oxide and titanium-zirconium oxide.

2. The method of claim 1 wherein said nanocrystals are capped with at least one agent to increase the solubility or dispersibility of said nanocrystals.

3. The method of claim 2 wherein said at least one agent comprises at least one organosilane, organocarboxylic acid or organoalcohol.

4. The method of claim 2 wherein said at least one agent to cap said nanocrystals is included in the solution.

5. The method of claim 4 wherein said at least one agent to cap said nanocrystals is contacted with said solution prior, during or after said reacting.

6. The method of claim 1 further comprising purifying and/or separating said nanocrystals.

7. The method of claim 6 further comprising capping said purified and/or separated nanocrystals with at least one capping agent to produce at least partially capped nanocrystals.

8. The method of claim 7 further comprising purifying and/or separating said at least partially capped nanocrystals.

9. The method of claim 6 further comprising contacting said purified and/or separated nanocrystals with a solvent.

10. The method of claim 8 further comprising contacting said at least partially capped nanocrystals with a solvent.

11. The method of claim 6 wherein said nanocrystals are dispersed in a further material.

12. The method of claim 11 wherein said further material is a polymer.

13. Nanocrystals formed by a method of claim 1.

14. A method of forming a film or coating comprising dispersing the nanocrystals of claim 13 in a further material to form a dispersion, and applying said dispersion to a surface.

15. The method of claim 14 wherein said applying comprises spin coating, spraying, dipping, screen printing, rolling, painting, printing, ink jet printing, depositing by evaporation and/or vapor deposition.

16. A method of forming a nanocomposite comprising combining the nanocrystals of claim 13 with a further material and forming the nanocomposite.

17. The method of claim 1 wherein said at least one solvent comprises benzyl alcohol, phenol, oleyl alcohol, toluene, butanol, propanol, isopropanol, ethanol, methanol, propylene glycol monomethyl ether (PGME), propylene glycol methyl ether acetate (PGMEA), ethyl lactate (EL), and 2-propoxy-propanol (PnP), acetonitrile, acetone, tetrahydrofuran, cyclic ketones and mixtures thereof.

18. The method of claim 2 wherein said at least one agent comprises at least one of n-propyltrimethoxysilane, n-propyltriethoxysilane, n-octyltrimethoxysilane, n-octyltriethoxysilane, phenytrimethoxysilane, 2-[methoxy(polyethyleneoxy)propyl]-trimethoxysilane, methoxytri(ethyleneoxy)propyltrimethoxysilane, 3-aminopropyltrimethoxysilane, 3-mercaptopropyltrimethoxysilane, 3-(methacryloyloxy) propyl trimethoxysilane, 3-isocyanatopropyltriethoxysilane, 3-isocyanatopropyltrimethoxysilane, and glycidoxypropyltrimethoxysilane, heptanol, hexanol, octanol, benzyl alcohol, phenol, ethanol, propanol, butanol, oleylalcohol, dodecylalcohol, octadecanol and triethylene glycol monomethyl ether, octanoic acid, acetic acid, propionic acid, 2-[2-(2-methoxyethoxy)ethoxy] acetic acid, oleic acid, benzoic acid or a mixture thereof.

19. The method of claim 11 wherein said further material comprises a fluoroplastic, a polyacrylate (Acrylic), a polyamide (PA or Nylon), a polyamide-imide (PAI), a polyketone (PK), a polyester, a polyimide (PI), a polysulfone (PSU), a polyurethane (PU), a spin-on-glass (SOG) polymer, a silicone, or mixtures thereof.

20. The method of claim 1 wherein said water is present at a molar ratio of water to precursor in a range from 1:1 to 4:1.

21. The method of claim 20 wherein said nanocrystals are in the average size range of 1 nm to 5 nm.

22. At least partially capped nanocrystals formed by a method of claim 7.

23. A method of forming a film or coating comprising dispersing the at least partially capped nanocrystals of claim 22 in a further material to form a dispersion, and applying said dispersion to a surface.

24. The method of claim 23 wherein said applying comprises spin coating, spraying, dipping, screen printing, rolling, painting, printing, ink jet printing, depositing by evaporation and/or vapor deposition.

25. A method of forming a nanocomposite comprising combining the at least partially capped nanocrystals of claim 22 with a further material and forming the nanocomposite.

26. The method of claim 7 wherein said at least partially capped nanocrystals are dispersed in a further material.

27. The method of claim 26 wherein said further material is a polymer.

28. The method of claim 26 wherein said further material comprises a fluoroplastic, a polyacrylate (Acrylic), a polyamide (PA or Nylon), a polyamide-imide (PAI), a polyketone (PK), a polyester, a polyimide (PI), a polysulfone (PSU), a polyurethane (PU), a spin-on-glass (SOG) polymer, a silicone or mixtures thereof.

29. The method of claim 9 wherein said solvent comprises benzyl alcohol, phenol, oleyl alcohol, toluene, butanol, propanol, isopropanol, ethanol, methanol, propylene glycol monomethyl ether (PGME), propylene glycol methyl ether acetate (PGMEA), ethyl lactate (EL), and 2-propoxy-propanol (PnP), acetonitrile, acetone, tetrahydrofuran, cyclic ketones and mixtures thereof.

30. The method of claim 10 wherein solvent comprises benzyl alcohol, phenol, oleyl alcohol, toluene, butanol, propanol, isopropanol, ethanol, methanol, propylene glycol monomethyl ether (PGME), propylene glycol methyl ether acetate (PGMEA), ethyl lactate (EL), and 2-propoxy-propanol (PnP), acetonitrile, acetone, tetrahydrofuran, cyclic ketones and mixtures thereof.

31. The method of claim 2 further comprising purifying and/or separating said nanocrystals.

32. The method of claim 31 further comprising contacting said purified and/or separated nanocrystals with a solvent.

33. The method of claim 32 wherein said solvent comprises benzyl alcohol, phenol, oleyl alcohol, toluene, butanol, propanol, isopropanol, ethanol, methanol, propylene glycol monomethyl ether (PGME), propylene glycol methyl ether acetate (PGMEA), ethyl lactate (EL), and 2-propoxy-propanol (PnP), acetonitrile, acetone, tetrahydrofuran, cyclic ketones and mixtures thereof.

34. The method of claim 31 wherein said nanocrystals are dispersed in a further material.

35. The method of claim 34 wherein said further material comprises a fluoroplastic, a polyacrylate (Acrylic), a polyamide (PA or Nylon), a polyamide-imide (PAI), a polyketone (PK), a polyester, a polyimide (PI), a polysulfone (PSU), a polyurethane (PU), a spin-on-glass (SOG) polymer, a silicone or mixtures thereof.

36. The method of claim 11 wherein said further material comprises poly(acrylonitrile-butadiene-styrene) (ABS), poly (methyl methacrylate) (PMMA), celluloid, cellulose acetate, poly(ethylene-vinyl acetate) (EVA), poly(ethylene vinyl alcohol) (EVOH), polyacrylonitrile (PAN), polyaryletherketone (PAEK), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyethylene (PE), polyetheretherketone (PEEK), polyetherketoneketone (PEKK), polyetherimide (PEI), polyethersulfone (PES), polyethylenechlorinates (PEC), polylactic acid (PLA), polymethylpentene (PMP), polyphenylene oxide (PPO), polyphenylene sulfide (PPS), polyphthalamide (PPA), polypropylene (PP), polystyrene (PS), polytrimethylene terephthalate (PTT), polyvinyl acetate (PVA), polyvinyl chloride (PVC), polyvinylidene chloride (PVDC), poly(styrene-acrylonitrile) (SAN), a Siloxane-spin-on polymer, Polydimethylsiloxane (PDMS) or polymethylphenylsiloxane, or mixtures thereof.

37. The method of claim 26 wherein said further material comprises poly(acrylonitrile-butadiene-styrene) (ABS), poly(methyl methacrylate) (PMMA), celluloid, cellulose acetate, poly(ethylene-vinyl acetate) (EVA), poly(ethylene vinyl alcohol) (EVOH), polyacrylonitrile (PAN), polyaryletherketone (PAEK), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyethylene (PE), polyetheretherketone (PEEK), polyetherketoneketone (PEKK), polyetherimide (PEI), polyethersulfone (PES), polyethylenechlorinates (PEC), polylactic acid (PLA), polymethylpentene (PMP), polyphenylene oxide (PPO), polyphenylene sulfide (PPS), polyphthalamide (PPA), polypropylene (PP), polystyrene (PS), polytrimethylene terephthalate (PTT), polyvinyl acetate (PVA), polyvinyl chloride (PVC), polyvinylidene chloride (PVDC), poly(styrene-acrylonitrile) (SAN), a Siloxane-spin-on polymer, Polydimethylsiloxane (PDMS) or polymethylphenylsiloxane, or mixtures thereof.

38. The method of claim 34 wherein said further material comprises poly(acrylonitrile-butadiene-styrene) (ABS), poly(methyl methacrylate) (PMMA), celluloid, cellulose acetate, poly(ethylene-vinyl acetate) (EVA), poly(ethylene vinyl alcohol) (EVOH), polyacrylonitrile (PAN), polyaryletherketone (PAEK), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyethylene (PE), polyetheretherketone (PEEK), polyetherketoneketone (PEKK), polyetherimide (PEI), polyethersulfone (PES), polyethylenechlorinates (PEC), polylactic acid (PLA), polymethylpentene (PMP), polyphenylene oxide (PPO), polyphenylene sulfide (PPS), polyphthalamide (PPA), polypropylene (PP), polystyrene (PS), polytrimethylene terephthalate (PTT), polyvinyl acetate (PVA), polyvinyl chloride (PVC), polyvinylidene chloride (PVDC), poly(styrene-acrylonitrile) (SAN), a Siloxane-spin-on polymer, Polydimethylsiloxane (PDMS) or polymethylphenylsiloxane, or mixtures thereof.

* * * * *